US010327895B2

(12) United States Patent
Lozonschi et al.

(10) Patent No.: US 10,327,895 B2
(45) Date of Patent: Jun. 25, 2019

(54) PRESSURE DIFFERENTIAL ACTUATED PROSTHETIC MEDICAL DEVICE

(71) Applicants: Lucian Lozonschi, Madison, WI (US); Georg Lutter, Kiel (DE)

(72) Inventors: Lucian Lozonschi, Madison, WI (US); Georg Lutter, Kiel (DE)

(73) Assignee: VDYNE, LLC, Maple Grove, MN (US)

( * ) Notice: Subject to any disclaimer, the term of this patent is extended or adjusted under 35 U.S.C. 154(b) by 252 days.

(21) Appl. No.: 15/588,053

(22) Filed: May 5, 2017

(65) Prior Publication Data

US 2018/0318071 A1    Nov. 8, 2018

(51) Int. Cl.
*A61F 2/24* (2006.01)

(52) U.S. Cl.
CPC .......... *A61F 2/2418* (2013.01); *A61F 2/2409* (2013.01); *A61F 2/2412* (2013.01); *A61F 2/2421* (2013.01); *A61F 2/2469* (2013.01); *A61F 2/2487* (2013.01); *A61F 2/2427* (2013.01); *A61F 2/2457* (2013.01); *A61F 2210/0014* (2013.01); *A61F 2210/0061* (2013.01); *A61F 2220/0008* (2013.01); *A61F 2230/0065* (2013.01); *A61F 2230/0069* (2013.01); *A61F 2230/0078* (2013.01); *A61F 2250/006* (2013.01); *A61F 2250/0069* (2013.01)

(58) Field of Classification Search
CPC ........ A61F 2/24; A61F 2/2409; A61F 2/2412; A61F 2/2418; A61F 2/2469; A61F 2/2487; A61F 2/2457; A61F 2210/0014; A61F 2220/0008; A61F 2230/0065; A61F 2230/0069; A61F 2230/0078; A61F 2250/006; A61F 2250/0069
See application file for complete search history.

(56) References Cited

U.S. PATENT DOCUMENTS

2004/0117009 A1*    6/2004   Cali ..................... A61F 2/2412
                                                 623/2.12

* cited by examiner

*Primary Examiner* — Katherin M Rodjom
(74) *Attorney, Agent, or Firm* — Juneau & Mitchell; Todd L. Juneau

(57) ABSTRACT

The invention relates to a medical prosthesis, and in particular a heart valve substitute comprising a pliant tubular conduit mounted on a resilient annular frame and tethered to a non-perforating anchor within the right or left ventricle of the heart, wherein the pliant tubular conduit is a reciprocating mechanical member that is compressed by pressurized working fluid within the ventricle during systole.

16 Claims, 38 Drawing Sheets

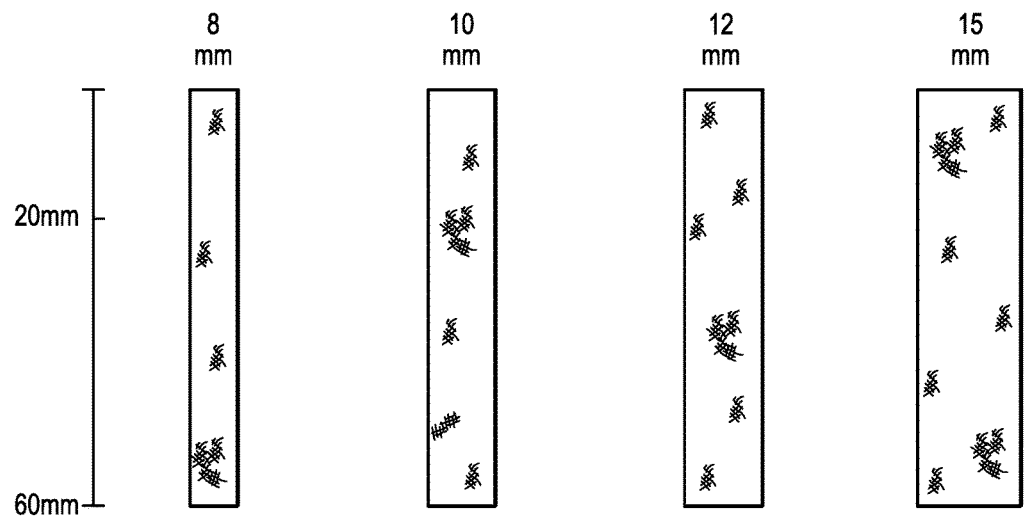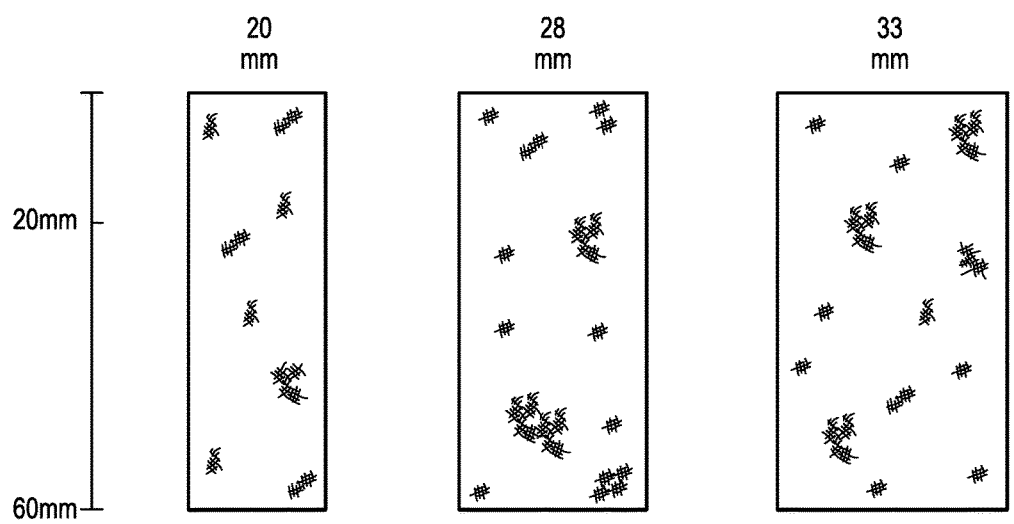

FIG. 10
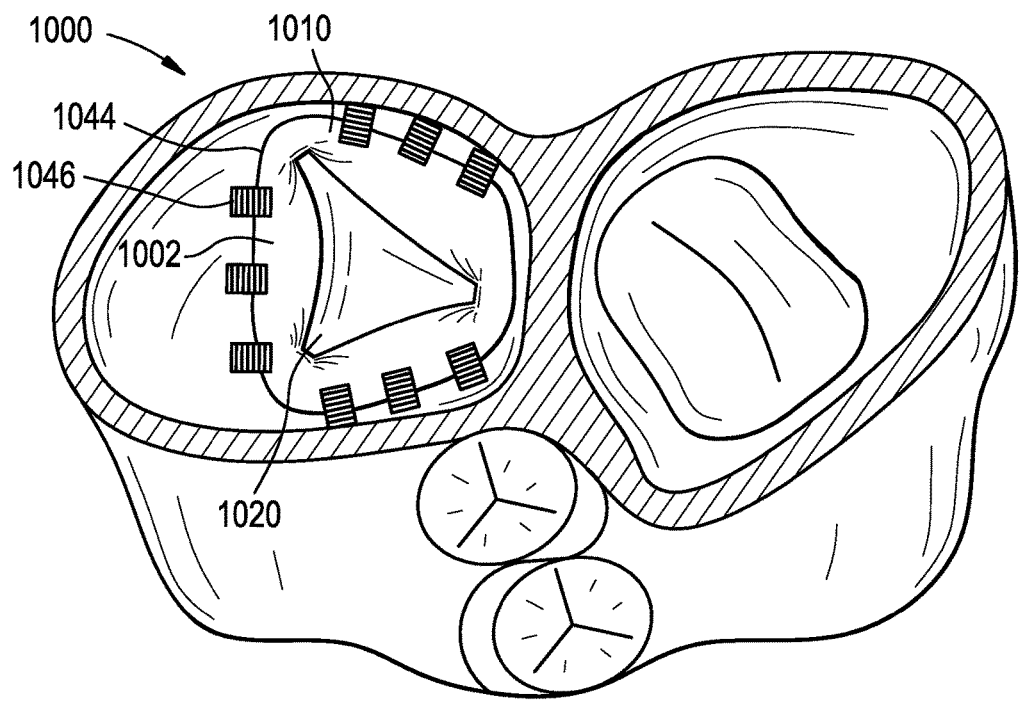
FIG. 11A  FIG. 11B
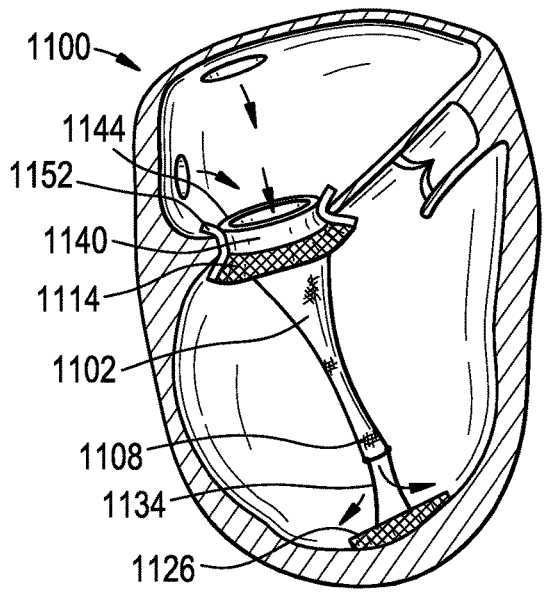
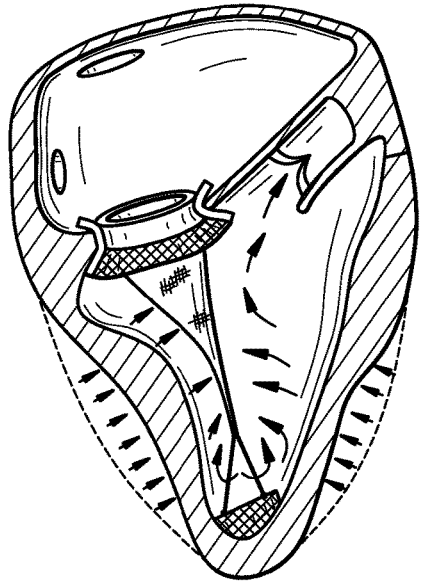

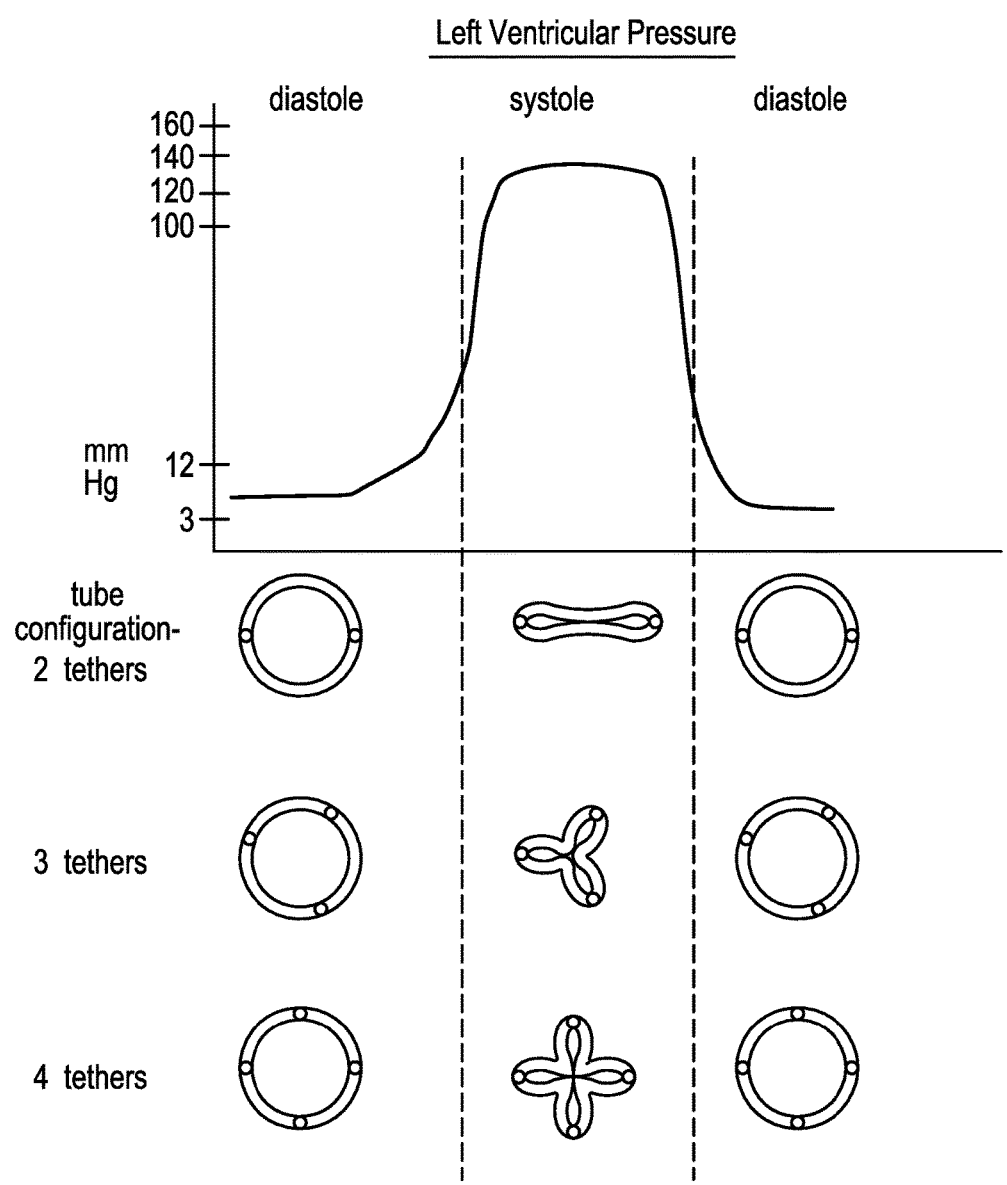

FIG. 14A
FIG. 14B
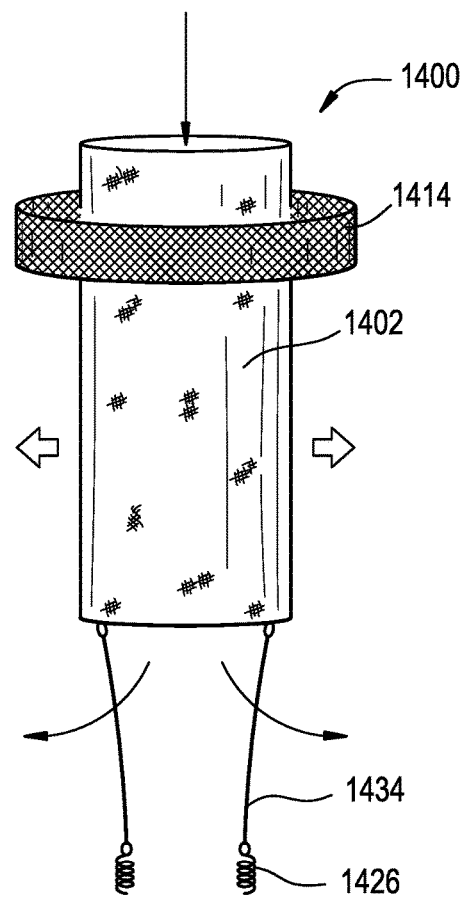
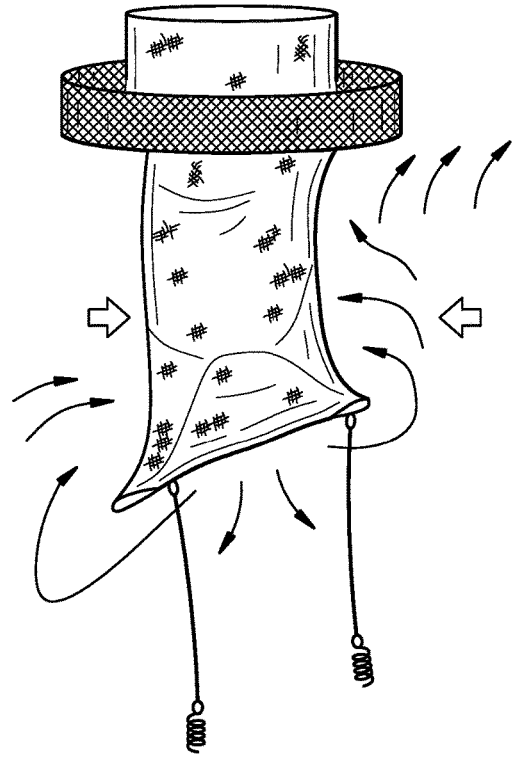

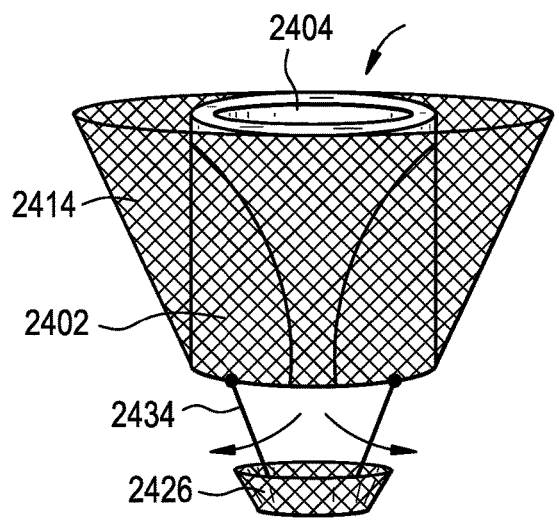
FIG. 24A
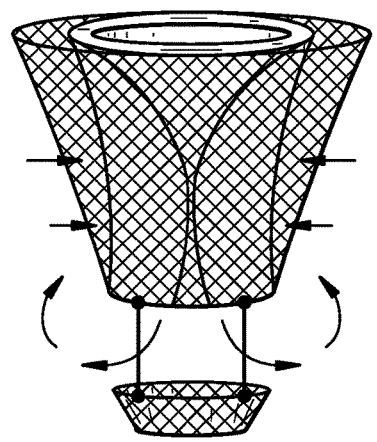
FIG. 24B
FIG. 25A
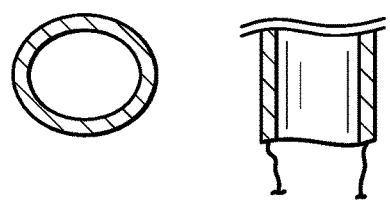
FIG. 25B
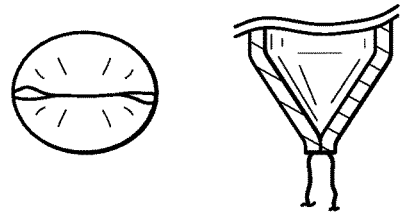
FIG. 25C
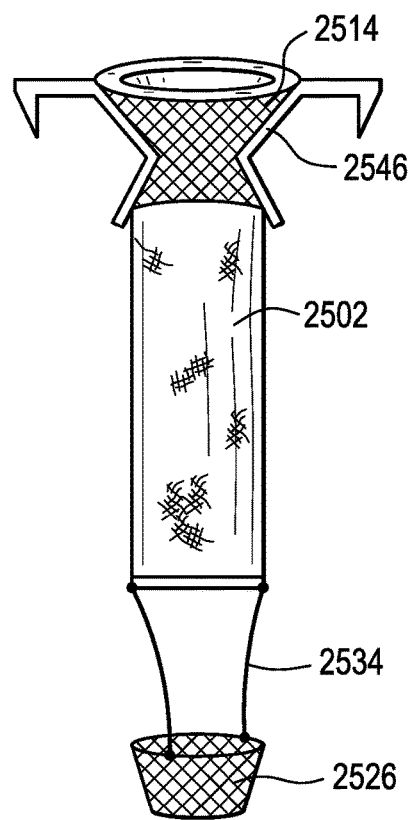

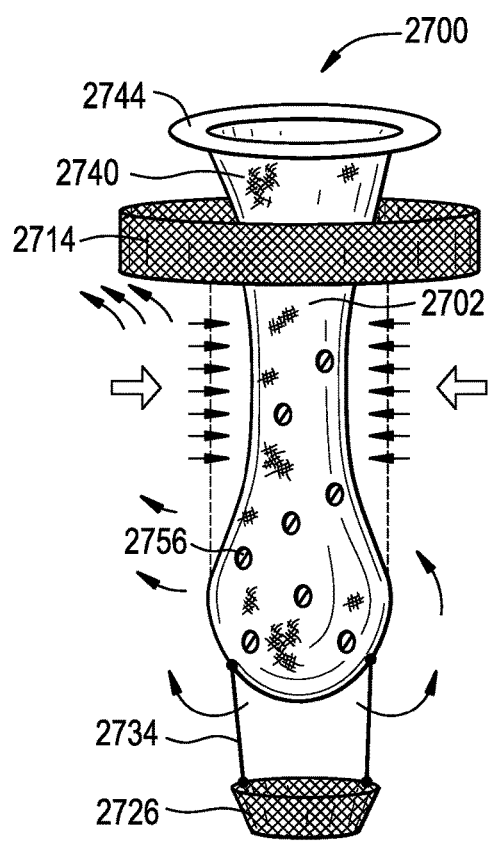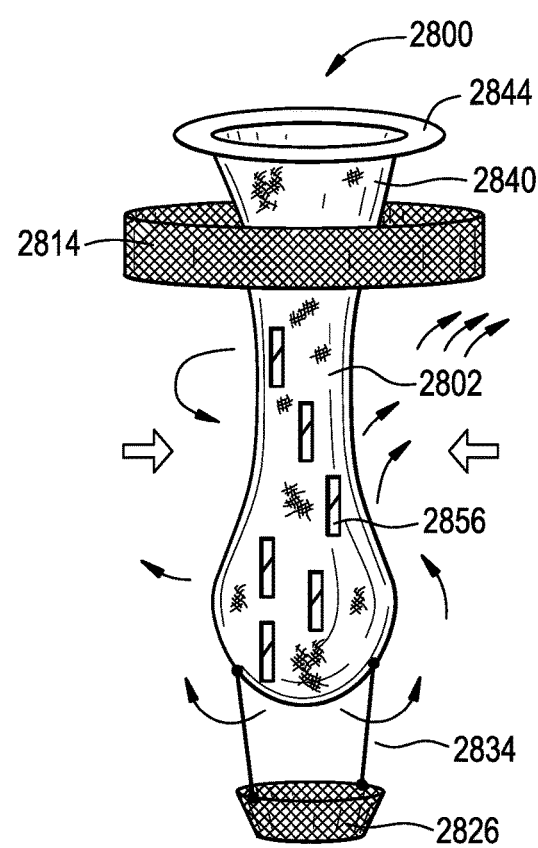

RV Diastole

RV Systole

PRESSURE DIFFERENTIAL ACTUATED PROSTHETIC MEDICAL DEVICE

CROSS-REFERENCE TO RELATED APPLICATIONS

Provided per USPTO rules by Application Data Sheet.

STATEMENT REGARDING FEDERALLY SPONSORED R&D

Provided per USPTO rules by Application Data Sheet.

NAMES OF PARTIES TO JOINT RESEARCH AGREEMENT

Provided per USPTO rules by Application Data Sheet.

REFERENCE TO SEQUENCE LISTING

Provided per USPTO rules by Application Data Sheet.

STATEMENT RE PRIOR DISCLOSURES

Provided per USPTO rules by Application Data Sheet.

BACKGROUND OF THE INVENTION

Field of the Invention

The invention relates to a medical prosthesis (Class 623), and in particular a heart valve substitute comprising a pliant tubular conduit (sub. 23.64) mounted on a resilient (sub. 2.14) annular frame (sub. 2.38) and tethered to a non-perforating anchor within the right or left ventricle of the heart, wherein the pliant tubular conduit is a reciprocating mechanical member (sub. 3.17) that is compressed by pressurized working fluid (sub. 3.20) within the ventricle during systole.

DESCRIPTION OF THE RELATED ART

In 1952 surgeons implanted the first mechanical heart valve. This first valve was a ball valve and it was designed by Dr. Charles Hufnagel. The recipient of this valve was a 30-year-old woman who could lead a normal life after the surgery. However, one downside of this design was that it could only be placed in the descending aorta instead of the heart itself. For this reason it did not fully correct the valve problem, only alleviate the symptoms. However it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting dic technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement. Additionally, stent-style replacement valves often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

Accordingly, the present invention is directed to a medical prosthesis, and in particular a heart valve substitute comprising a pliant tubular conduit that is mounted on a resilient annular or sub-annular frame and that is tethered to a non-perforating anchor within the right or left ventricle of the heart, wherein the pliant tubular conduit is a reciprocating mechanical member that is compressed by pressurized working fluid, blood, within the ventricle during systole. Importantly, this heart valve substitute has no leaflets and does not have a traditional valve configuration. Additionally, the device can be delivered to the ventricle compressed within a catheter, and expelled from the catheter to be deployed without open heart surgery.

The invention provides in one preferred embodiment a prosthetic medical device, comprising: (i) an elongated flexible cylinder defining a channel therein, said channel having a volume that ranges from 1.57 mL-18.84 mL, said cylinder having an average radius of 4.0-16.5 mm and an average height of 20-60 mm, said cylinder comprised of decellularized pericardium, said cylinder having top end, a bottom end, an internal surface, and an external surface, said cylinder is compressible under a pressure of 100-160 mm Hg on the external surface to close the channel, and said cylinder is expandable under a pressure of 40-80 mm Hg on the internal surface to open the channel; (ii) a one-piece, laser-cut, expandable nitinol top stent, said top stent attached to the top end of the cylinder, said top stent shaped as a conic frustum when expanded and defining a top stent channel therein, said conic frustum having a side wall, a top aperture, and a bottom aperture, said side wall having an average side length of 5-20 mm, said top aperture having an average expanded diameter of 30-35 mm, said bottom aperture having an average expanded diameter of 40-60 mm, said top stent having a cover, said cover connected with the cylinder wherein the channel of the cylinder is in communication with the top stent channel; and (iii) a one-piece, laser-cut, expandable nitinol bottom stent, said bottom stent having a top end, a bottom end, and a side wall, said top end of the bottom stent having from 2-5 tethers attached to the bottom end of the cylinder, said bottom stent having an average expanded diameter of 20-35 mm.

In another preferred embodiment, there is provided a prosthetic medical device as described and claimed herein wherein the cylinder is shaped as a conic cylinder, said top end having a diameter of 30-35 mm and said bottom end having a diameter of 8-20 mm.

In another preferred embodiment, there is provided a prosthetic medical device as described and claimed herein wherein the top stent cover is comprised of polyethylene terephthalate, decellularized pericardium, or a layered combination thereof.

In another preferred embodiment, there is provided a prosthetic medical device as described and claimed herein wherein the top end of the cylinder comprises, in order, a top edge connected to a top spacer segment that is connected to a top stent mounting segment, wherein the top edge has an collar mounted around the circumference of the top edge, said collar arranged as a flexible, semi-rigid, substantially flat panel or flat disk and having an average diameter of 30-60 mm, said collar having a nitinol frame covered with polyethylene terephthalate, decellularized pericardium, or a layered combination thereof, wherein the top spacer segment of the cylinder has a height from 5-20 mm, and wherein the top stent is mounted circumferentially around the top stent mounting segment of the cylinder.

In another preferred embodiment, there is provided a prosthetic medical device as described and claimed herein wherein the collar has one or more tissue anchors arranged along the circumference of the collar.

In another preferred embodiment, there is provided a prosthetic medical device as described and claimed herein wherein the nitinol frame of the collar supports a gel ring, wherein the gel ring is comprised of an expandable material enclosed within an outer sealing membrane, wherein the expandable material is a swellable powder within a polymeric matrix, a swellable polymeric matrix, or a swellable polymeric liquid.

In another preferred embodiment, there is provided a prosthetic medical device as described and claimed herein wherein the nitinol frame of the collar supports a deflatable ring, wherein the deflatable ring is comprised of a toroid-shaped sealed compartment having a valve, said sealed compartment fillable with a biocompatible liquid or gas, wherein upon removal of some or all of the biocompatible liquid or gas, the deflatable ring has a reduced diameter, and wherein upon removal of some or all of the biocompatible liquid or gas, the top spacer segment of the cylinder has a reduced height and the collar is compressed in the direction of the top stent.

In another preferred embodiment, there is provided a prosthetic medical device as described and claimed herein wherein the top stent has one or more tissue anchors arranged along the side wall of the top stent.

In another preferred embodiment, there is provided a prosthetic medical device as described and claimed herein wherein the bottom stent has one or more tissue anchors arranged along the side wall of the bottom stent.

In another preferred embodiment, there is provided a prosthetic medical device as described and claimed herein wherein the cylinder has an hourglass (hyperboloid) shape from top end to bottom end.

In another preferred embodiment, there is provided a prosthetic medical device as described and claimed herein wherein the bottom end of the cylinder is sealed, and wherein the cylinder has one or more perforations in a mid-segment side wall of the cylinder.

In another preferred embodiment, there is provided a prosthetic medical device as described and claimed herein wherein the top stent comprises a central stent hub with aperture and having a top circumferential flange and a bottom circumferential flange connected to the hub, with a top toroidal inflatable ring attached to the top circumferential flange and a bottom toroidal inflatable ring attached to the bottom circumferential flange.

In another preferred embodiment, there is provided a prosthetic medical device as described and claimed herein wherein the top stent comprises a threaded structure on an exterior surface of the stent, wherein the threaded structure allows for a simple circular screw-type deployment of the device into a native annulus to aid in sealing and sizing of the top stent into the native annulus.

In a preferred embodiment, there is also provided a method of controlling flow of bodily fluid within an enclosed cavity of a human body, said enclosed cavity having a reciprocating pressure differential, the method comprising the steps: (i) delivering the prosthetic medical device of claim 1 to the enclosed cavity within the human body; (ii) arranging the prosthetic medical device of claim 1 whereby the cylinder and cylinder channel are arranged parallel to a flow of fluid entering the enclosed cavity; (iii) expanding the top stent within an entrance to the enclosed cavity to mount the top end of the cylinder within the entrance, and whereby the side wall of the top stent applies an axial compression force and seals the entrance; (iv) expanding the bottom stent within the enclosed cavity to anchor the bottom end of the cylinder; wherein bodily fluid arriving at the enclosed cavity is diverted into the channel of the cylinder; wherein the reciprocating pressure differential comprises a low pressure state and a high pressure state; wherein bodily fluid flows into the channel to the enclosed cavity during the low pressure state, and wherein bodily fluid is prevented from flowing into the channel to the enclosed cavity during the high pressure state, wherein the high pressure state exerts a force on the external surface of the cylinder and collapses the reversibly collapses the channel.

In another preferred embodiment, there is provided a method as described and claimed herein further comprising the step of anchoring the prosthetic medical device of claim 1 to tissue within the enclosed cavity.

In another preferred embodiment, there is provided a medical prosthesis as claimed and described herein wherein the medical prosthesis is a heart valve substitute and comprises a pliant tubular conduit that is mounted on a resilient annular or sub-annular frame, the conduit is tethered to a non-perforating anchor for deployment within a right or left ventricle of a heart, wherein the pliant tubular conduit is a reciprocating mechanical member that is compressed by pressurized working fluid within the ventricle during a high pressure phase of the heart (systole).

In another preferred embodiment, there is provided a medical prosthesis as claimed and described herein wherein the medical prosthesis is a heart valve substitute comprising a pliant tubular conduit that is mounted on a resilient expandable passive assist cage, the cage is deployed within an atrial or ventricular chamber of a heart, wherein the pliant tubular conduit is a reciprocating mechanical member that is compressed by pressurized working fluid within the ventricle during a high pressure phase of the heart (systole).

In another preferred embodiment, there is provided a medical prosthesis as claimed and described herein wherein the cage defines an interior cavity and the conduit is mounted within the cavity.

In another preferred embodiment, there is provided a medical prosthesis as claimed and described herein wherein the cage defines an interior cavity and the conduit is mounted outside of the cavity.

In another preferred embodiment, there is provided a medical prosthesis as claimed and described herein wherein the medical prosthesis comprises a prosthetic valve that is mounted on a resilient expandable passive assist cage, the passive assist cage is deployed within an atrial or ventricular chamber of a heart, wherein the prosthetic valve is a reciprocating mechanical member that is closed by pressurized working fluid within the ventricle during a high pressure phase of the heart (systole) and opened by lower pressure working fluid within the ventricle during a low pressure phase of the heart (diastole).

BRIEF DESCRIPTION OF THE SEVERAL VIEWS OF DRAWING

FIG. 3 is a multi-feature illustration of a various sizes of unassembled top stents, cylinders, tethers, and bottom stents, and also showing a exemplary prosthetic medical device as described and claimed herein. FIG. 3(a)-(d) are illustrations of top stents, FIG. 3(e) is an illustration of a stent cover, FIG. 3(f)-(l) are illustrations of elongated flexible cylinders, FIG. 3(m)-(n) are illustrations of bottom stents, FIG. 3(o)-(p) are illustrations of tethers, FIG. 3(q) is a placement schematic for the right atrium and right ventricle and shows the channel axis, and FIG. 3(r) is an illustration of exemplary prosthetic medical device as described and claimed herein.

Figure 4A:
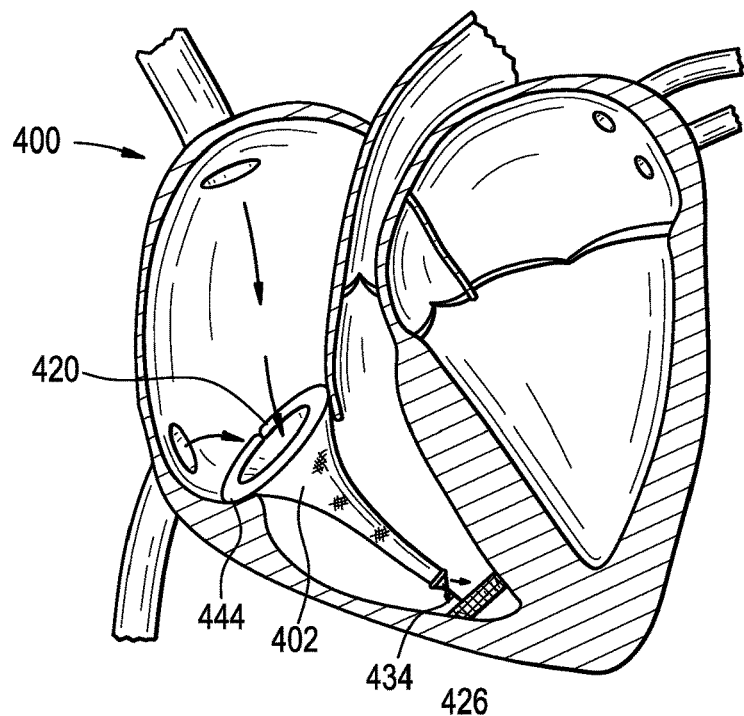
Figure 4B:
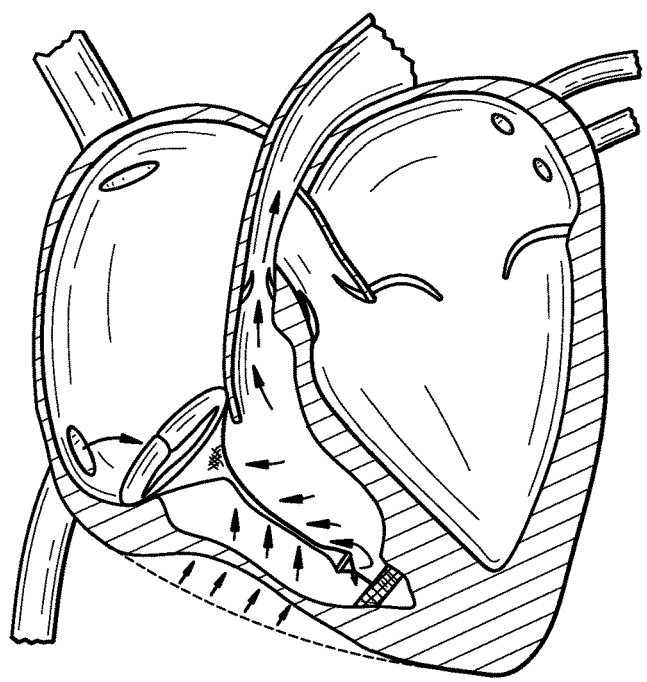

FIGS. 4(a) and 4(b) are illustrations showing one embodiment of the present prosthetic medical device deployed in a cross-sectional representation of a right atrium and right ventricle. FIGS. 4(a) and (b) show a time sequence of a funnel-shaped intra-ventricular cylinder being compressed by systolic action of the right ventricle on the intraventricular blood.

Figure 5A:
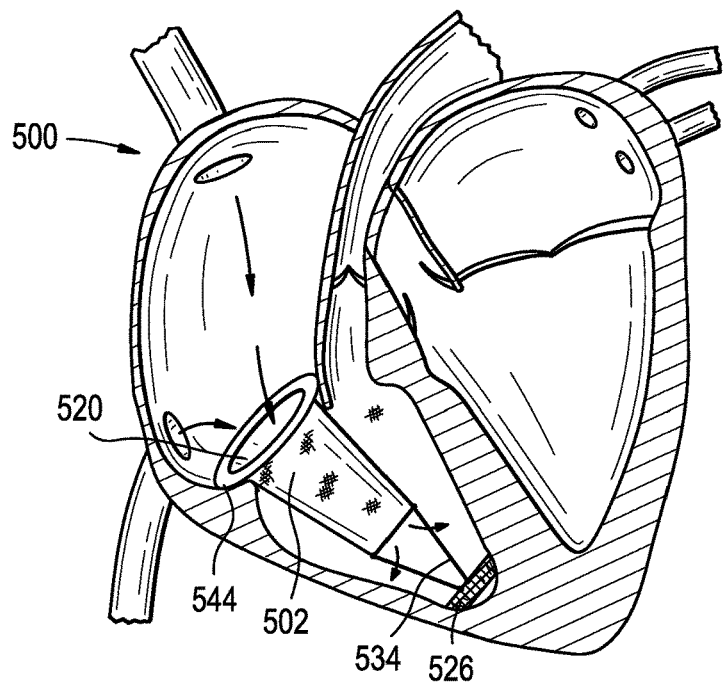
Figure 5B:
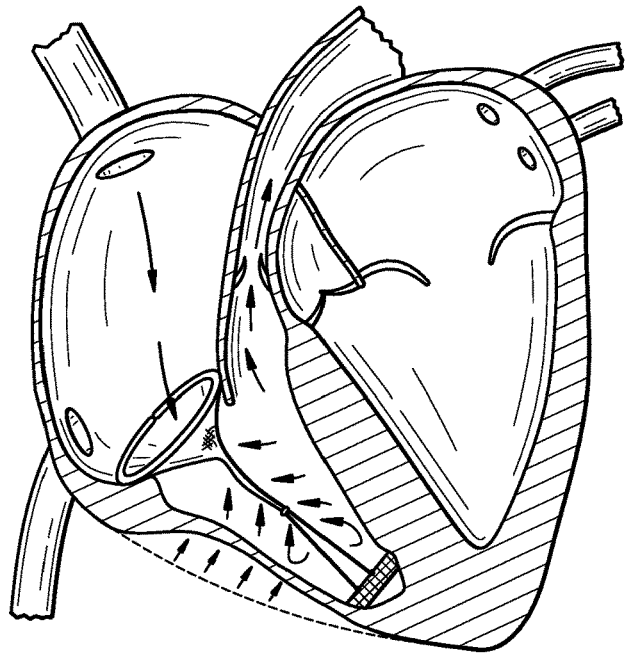

FIGS. 5(a) and 5(b) are illustrations showing one embodiment of the present prosthetic medical device deployed in a cross-sectional representation of a right atrium and right ventricle. FIGS. 5(a) and (b) show a time sequence of a conic-shaped intra-ventricular cylinder being compressed by systolic action of the right ventricle on the intraventricular blood.

Figure 6A:
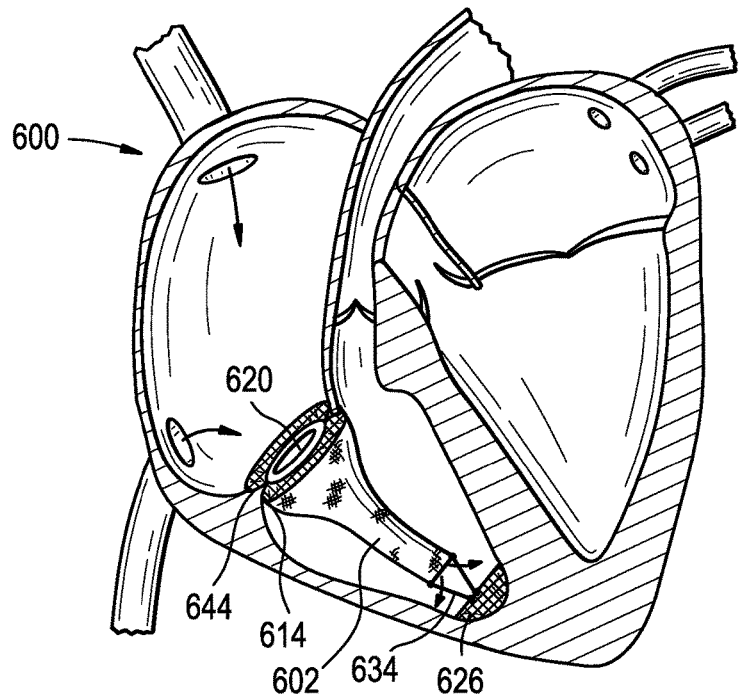
Figure 6B:
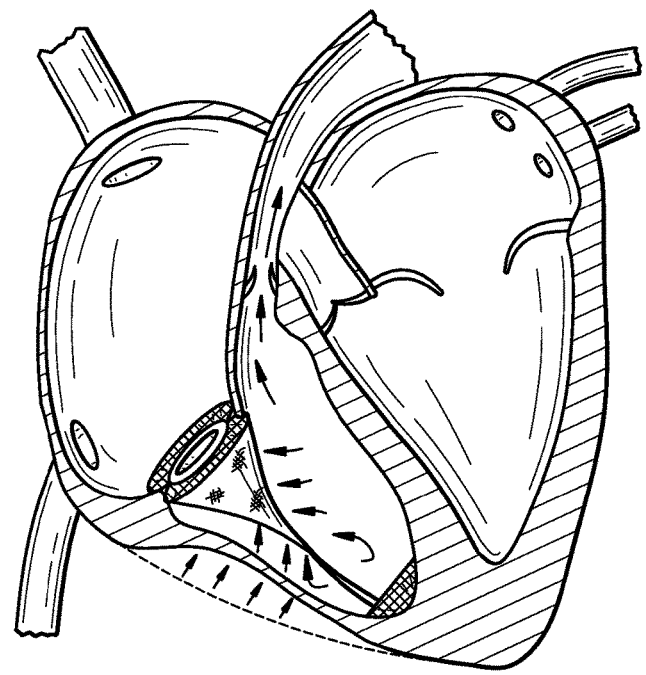

FIGS. 6(a) and 6(b) are illustrations showing one embodiment of the present prosthetic medical device deployed in a cross-sectional representation of a right atrium and right ventricle. FIGS. 6(a) and (b) show a time sequence of a funnel-shaped intra-ventricular cylinder being compressed by systolic action of the right ventricle on the intraventricular blood. FIGS. 6(a) and (b) also show an example of a device having a partial atrial collar.

Figure 7A:
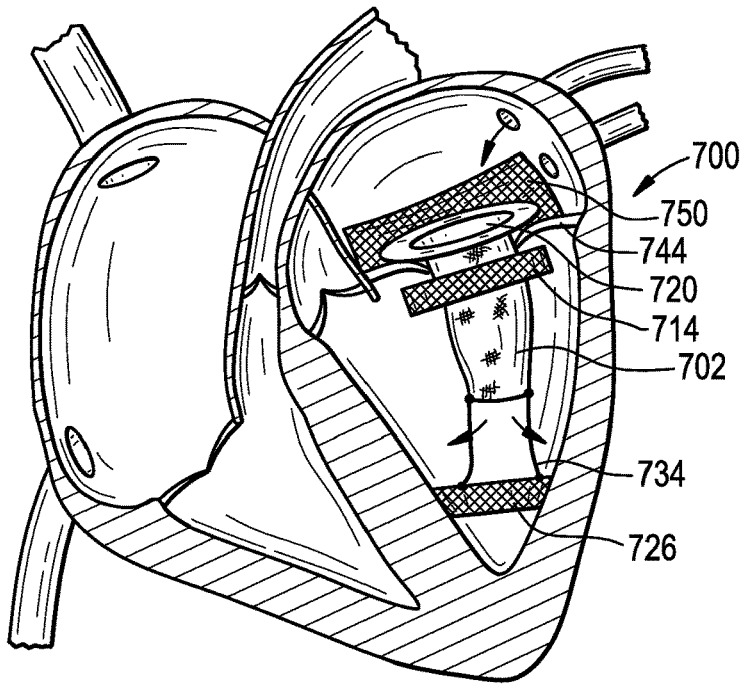
Figure 7B:
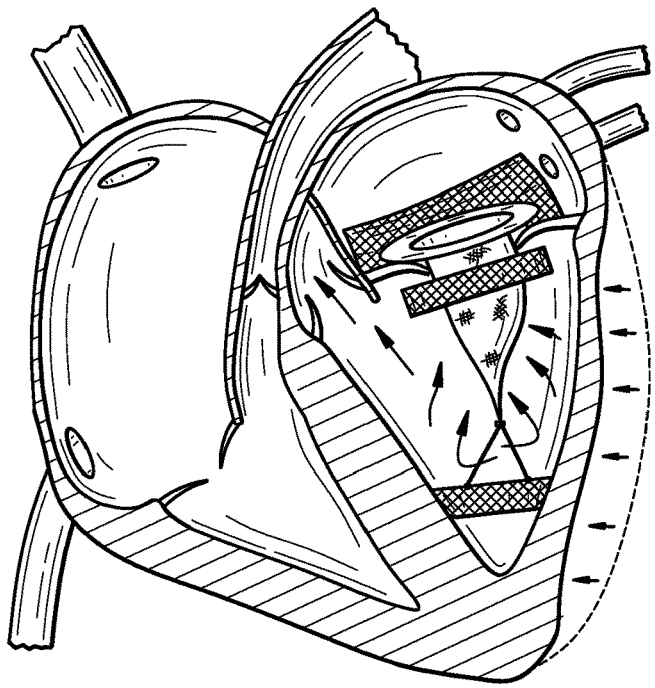

FIGS. 7(a) and 7(b) are illustrations showing one embodiment of the present prosthetic medical device deployed in a cross-sectional representation of a left atrium and left ventricle. FIGS. 7(a) and (b) show a time sequence of a conic-shaped intra-ventricular cylinder being compressed by systolic action of the left ventricle on the intraventricular blood. FIGS. 7(a) and 7(b) also illustrate a device having a larger panel-shaped atrial collar.

Figure 8:
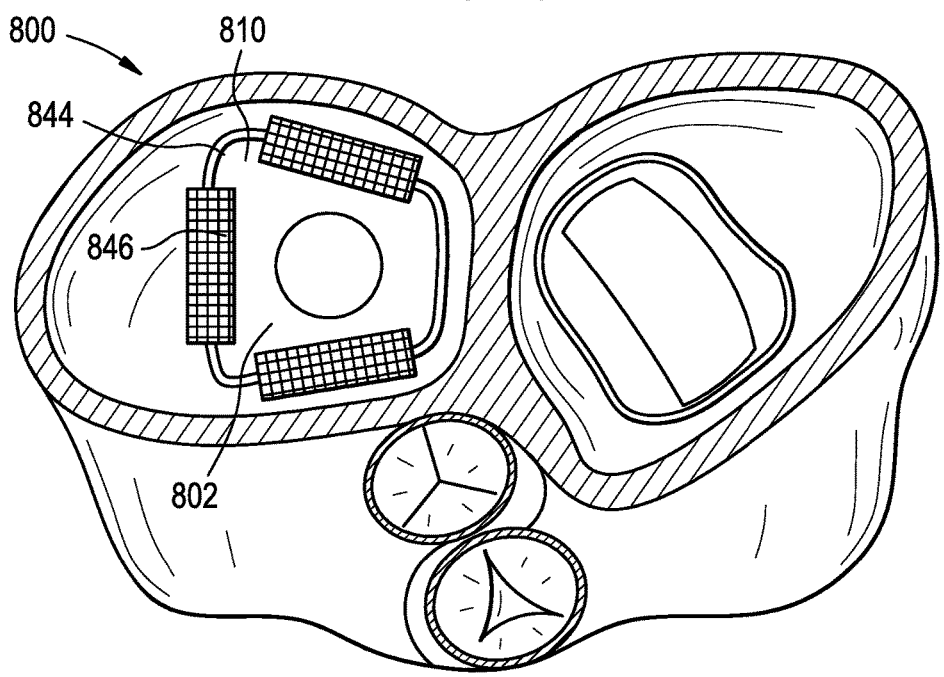

FIG. 8 is a mid-height horizontal cross-sectional illustration of a heart and shows a top atrial view of a collared embodiment of the present invention having three wide-variety leaflet-collar anchors.

Figures 9A, 9B:
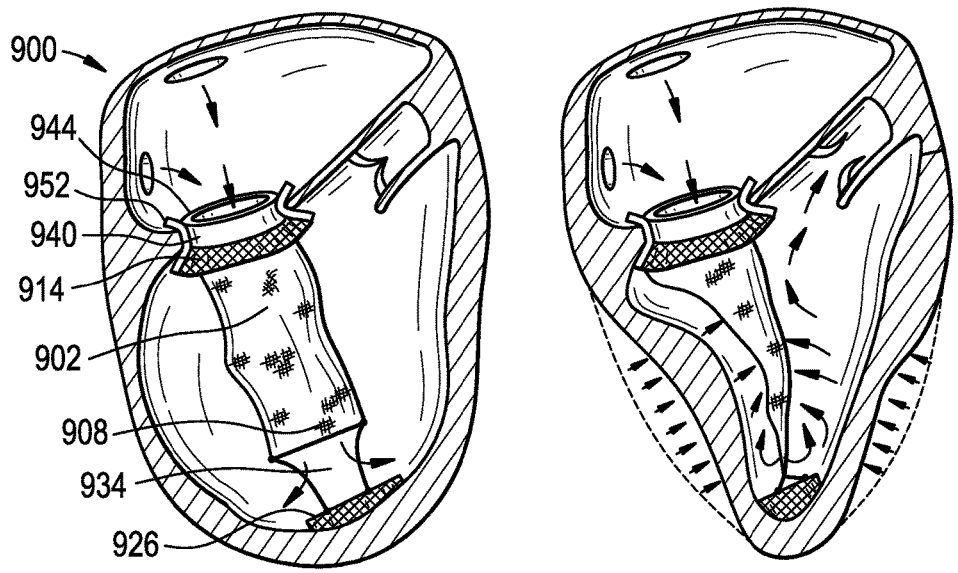

FIGS. 9(a) and 9(b) are illustrations showing one embodiment of the present prosthetic medical device deployed in a cross-sectional representation of a right atrium and right ventricle. FIGS. 9(a) and (b) show a time sequence of an intra-ventricular cylinder being compressed by systolic action of the right ventricle on the intraventricular blood. FIGS. 9(a) and (b) also illustrate perivalvular leaflet anchors at the septal and anterior positions that extend from atrium to ventricle.

FIG. 10 is a mid-height horizontal cross-sectional illustration of a heart and shows a top atrial view of a collared embodiment of the present invention having a triangular aperture and nine medium-width variety leaflet-collar anchors.

FIGS. 11(a) and 11(b) are illustrations showing one embodiment of the present prosthetic medical device deployed in a cross-sectional representation of a right atrium and right ventricle. FIGS. 11(a) and (b) show a time sequence of a funnel-shaped intra-ventricular cylinder being compressed by systolic action of the right ventricle on the intra-ventricular blood. FIGS. 11(a) and (b) also illustrate perivalvular leaflet anchors at the septal and anterior positions that extend from atrium to ventricle.

Figure 12:
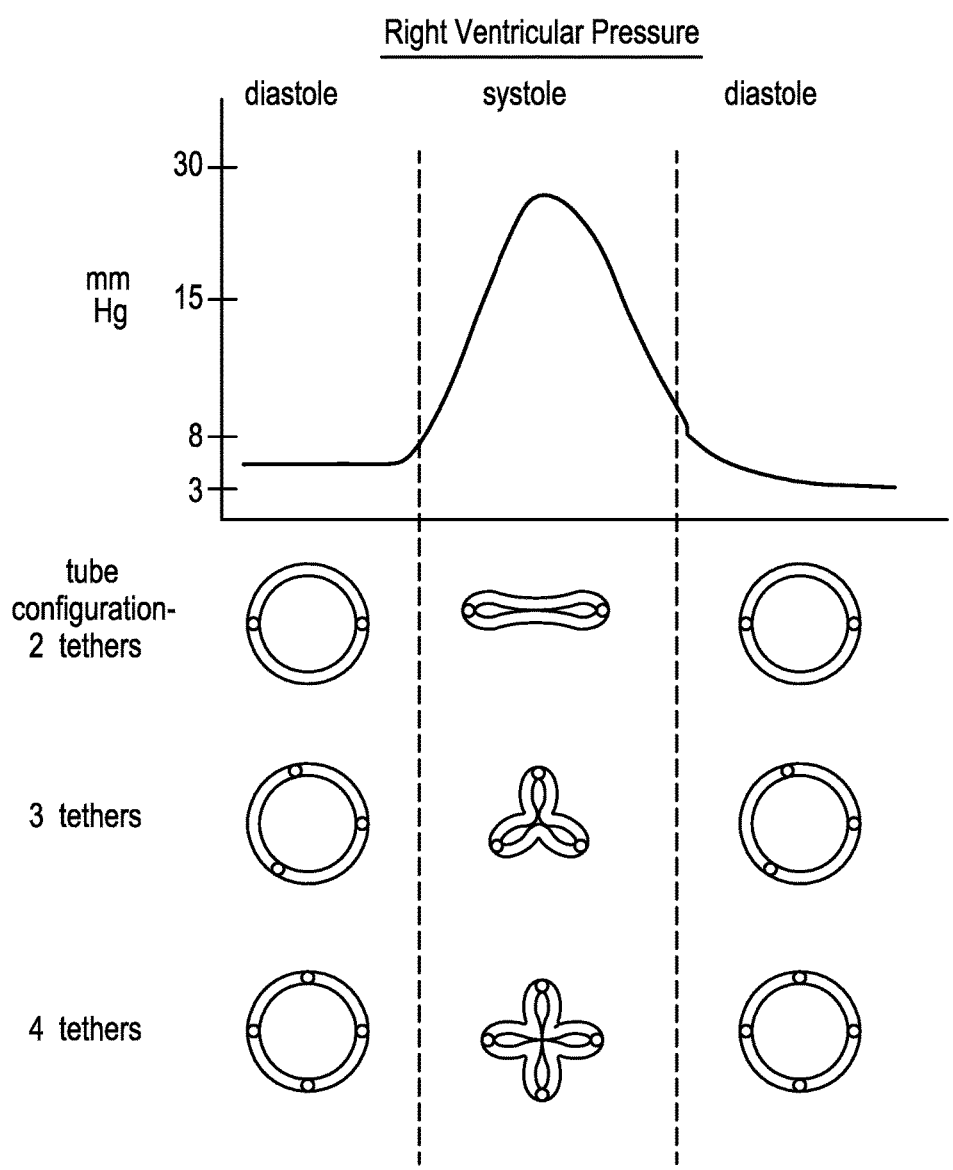

FIG. 12 is a graphic representation of the change in right ventricular pressure from diastole to systole to diastole. FIG. 12 shows the change in cross-sectional shape of the cylinder when a 2-, 3-, or 4-tether embodiment is deployed.

FIG. 13 is a graphic representation of the change in left ventricular pressure from diastole to systole to diastole. FIG. 13 shows the change in cross-sectional shape of the cylinder when a 2-, 3-, or 4-tether embodiment is deployed.

FIGS. 14(a) and 14(b) are illustrations showing one embodiment of the present prosthetic medical device. FIGS. 14(a) and (b) show a time sequence of an intra-ventricular cylinder being compressed by hydro- or hemo-dynamic action of tissue that define a pressure cavity on the intracavity fluid. FIGS. 14(a) and (b) also illustrate a simple stent and cylinder device embodiment of the present invention having two tethers attached to tissue anchors.

Figure 15A:
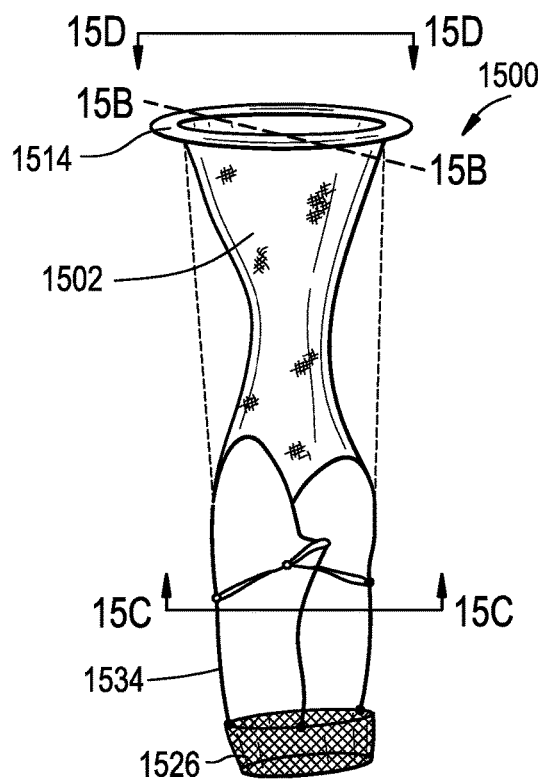
Figure 15B:
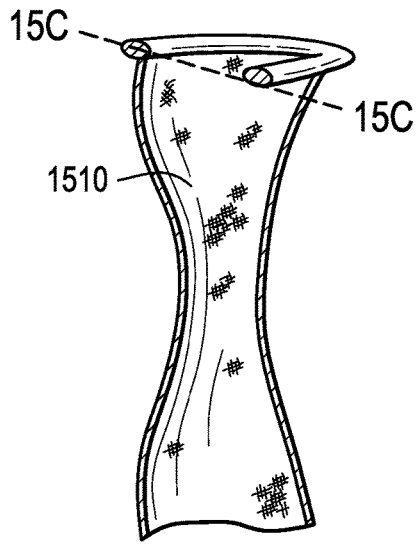
Figure 15C:
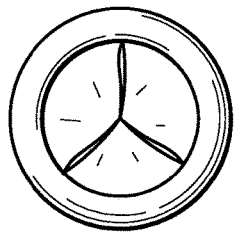
Figure 15D:
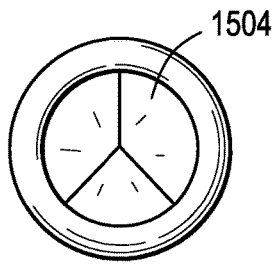

FIG. 15(a)-(d) is a multi-component view of an illustration of an hourglass-shaped, three-tether, cable-type top stent embodiment of the present invention. FIG. 15(a) shows an illustration of an entire device. FIG. 15(b) shows a cross-sectional view of just the top stent and cylinder along line C-C. FIG. 15(c) shows a bottom view along line B-B and shows how the cylinder collapses to a closed position. FIG. 15(d) shows a top view along line A-A looking down the interior of the channel.

Figure 16A:
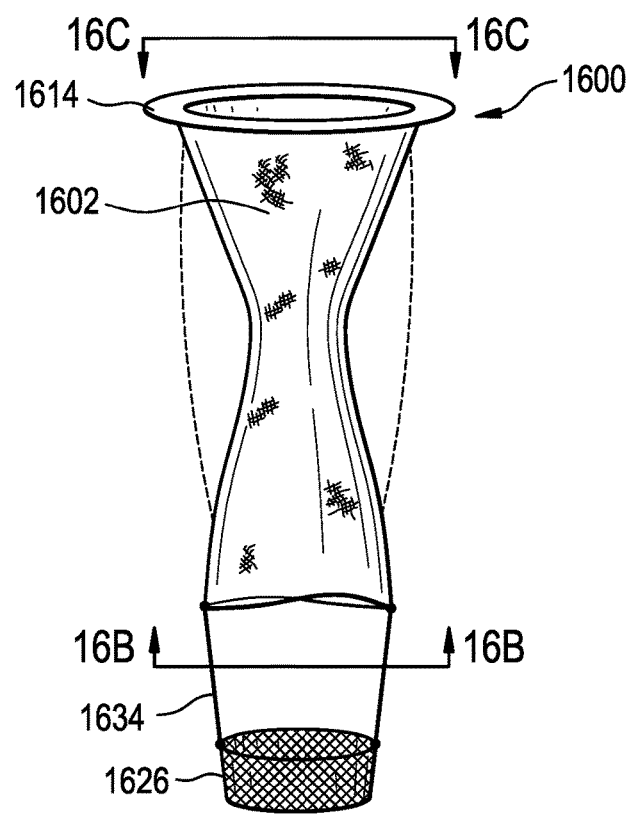
Figure 16B:
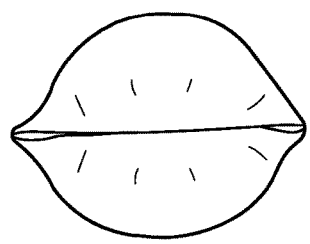
Figure 16C:
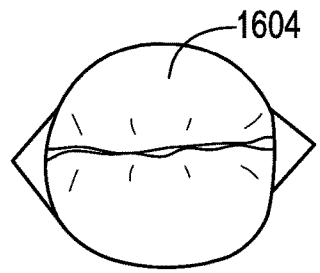

FIG. 16(a)-(c) is a multi-component view of an illustration of an hourglass-shaped, two-tether, cable-type top stent embodiment of the present invention. FIG. 16(a) shows an illustration of an entire device. FIG. 16(b) shows a bottom view along line B-B and shows how the cylinder collapses to a closed position. FIG. 16(c) shows a top view along line A-A looking down the interior of the channel.

Figure 17:
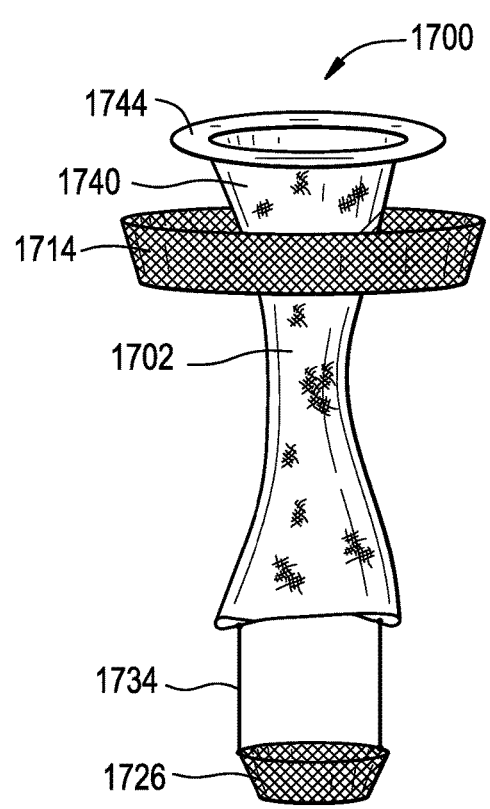

FIG. 17 is an illustration of another embodiment of the present device and shows a cable-style (toroidal) collar attached to an hourglass shaped cylinder that has a wide-aspect top stent mounted around the cylinder. FIG. 17 shows a two tether embodiment and a low-aspect bottom-stent style anchor.

Figure 18:
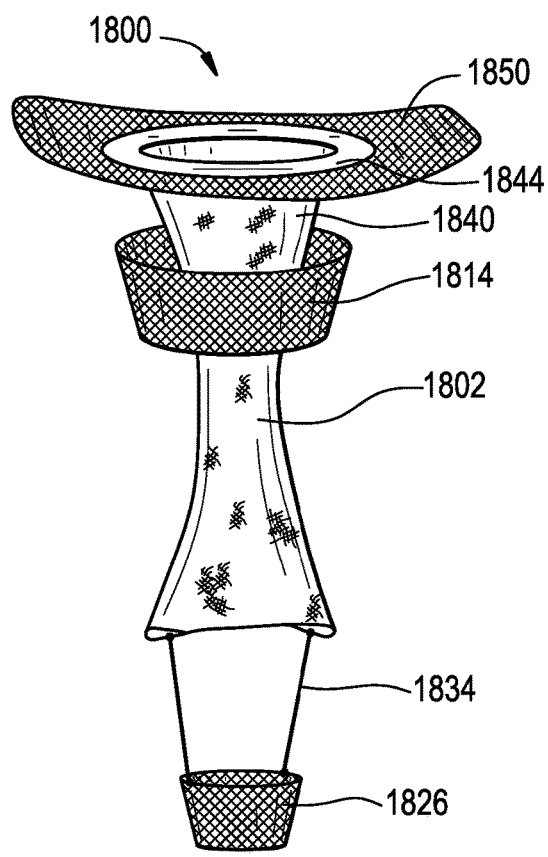

FIG. 18 is an illustration of another embodiment of the present device and shows a cable-style (toroidal) collar with a large panel attached to an hourglass shaped cylinder that has a narrow-aspect top stent mounted around the cylinder. FIG. 18 shows a two tether embodiment and a narrow-aspect bottom-stent style anchor.

Figure 19:
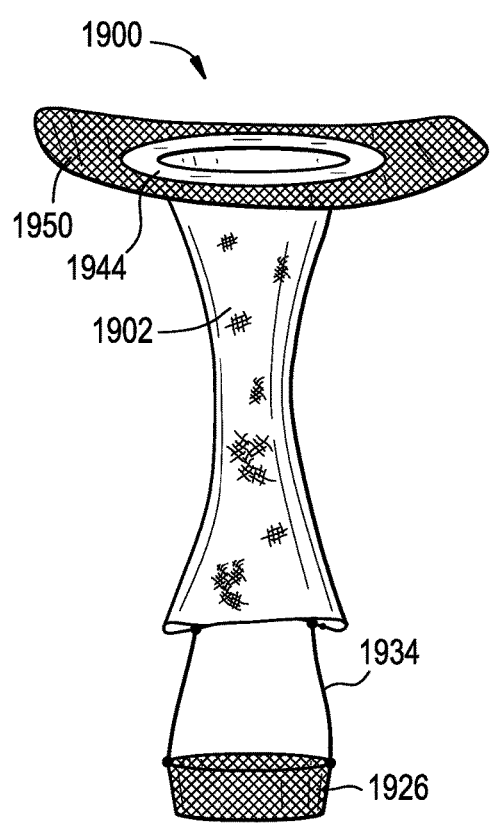

FIG. 19 is an illustration of another embodiment of the present device and shows a cable-style (toroidal) collar with a large panel attached to an hourglass shaped cylinder but does not have any top stent mounted around the cylinder. FIG. 19 shows a two tether embodiment and a low-aspect bottom-stent style anchor.

Figure 20:
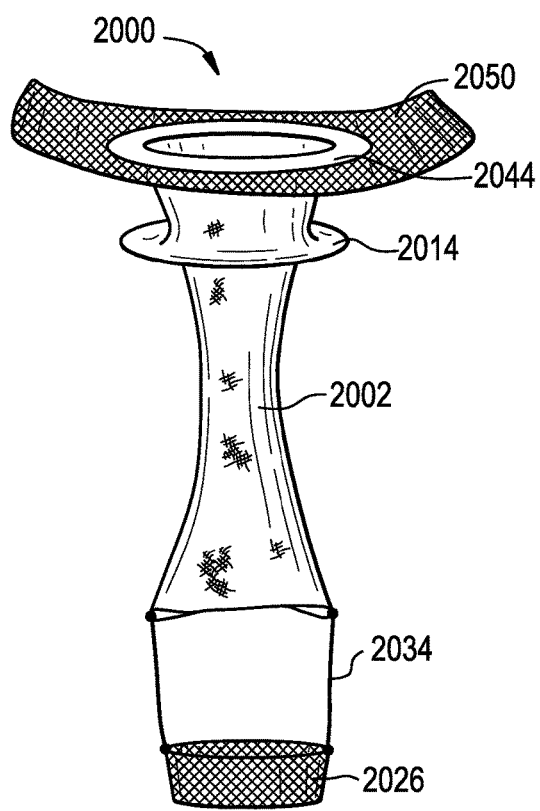

FIG. 20 is an illustration of another embodiment of the present device and shows a cable-style (toroidal) collar with a large panel attached to an hourglass shaped cylinder and has a covered-frame style top stent mounted around the cylinder. FIG. 20 shows a two tether embodiment and a low-aspect bottom-stent style anchor.

Figure 21A:
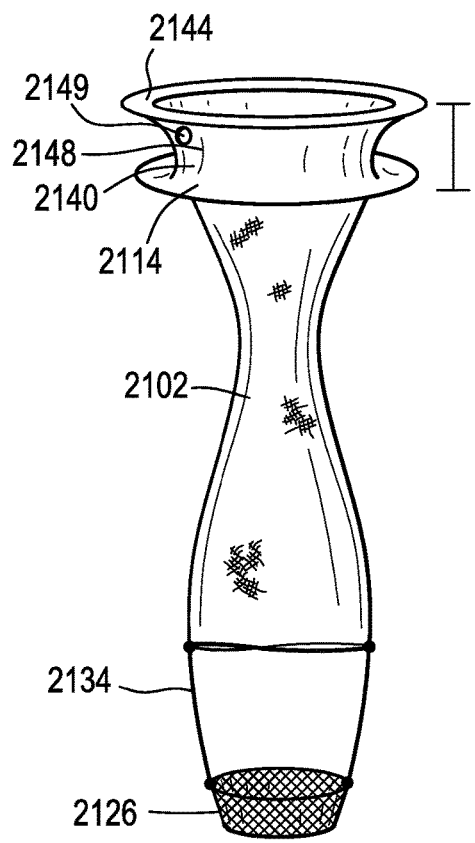
Figure 21B:
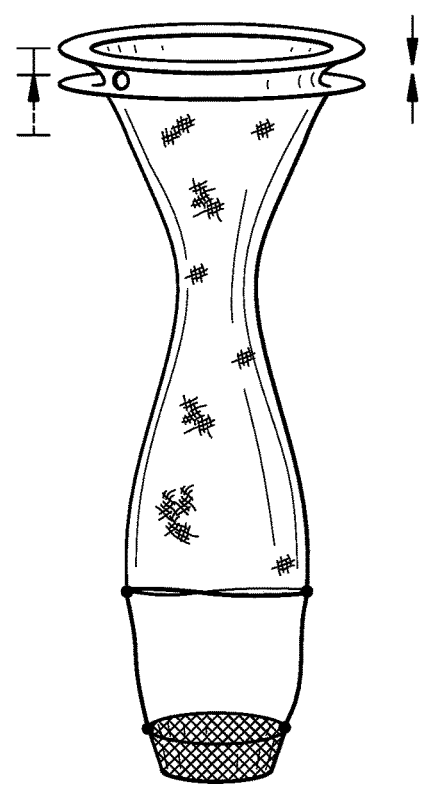
Figure 21C:
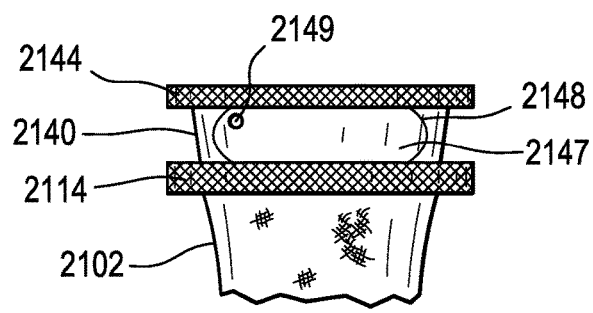

FIG. 21 is an illustration of another embodiment of the present device and shows a vacuum-mounting feature whereby a cable-style (toroidal) collar is attached to an hourglass shaped cylinder that has a covered-frame style top stent mounted around the cylinder, but where the top stent has a covered nitinol frame that supports a deflatable ring, wherein the deflatable ring is comprised of a toroid-shaped sealed compartment having a valve, said sealed compartment fillable with a biocompatible liquid or gas, wherein upon removal of some or all of the biocompatible liquid or gas, the deflatable ring works in cooperation with the (non-moving) collar to compress the top spacer segment of the cylinder to a reduced height and thereby operate to seal and mount the device within a native annulus. FIG. 21 shows a two tether embodiment and a low-aspect bottom-stent style anchor.

Figure 22A:
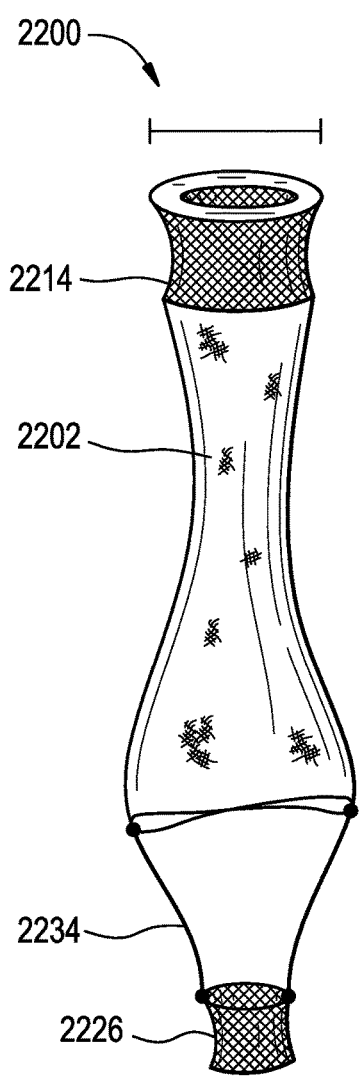
Figure 22B:
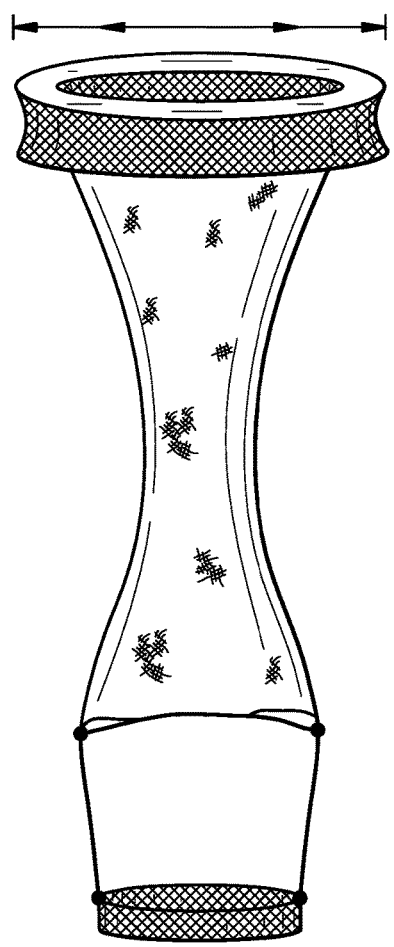

FIGS. 22(a) and 22(b) are illustrations of another embodiment of the present device and shows in sequence an expansion-mounting feature whereby a compressed top-stent is attached to an hourglass shaped cylinder but whereby the top-stent and the bottom stent are comprised of a compressed material that is released, or of an inelastic deformable material, and thereby operate to seal and mount the device within a native annulus and native mount-area. FIG. 22 shows a two tether embodiment and a low-aspect bottom-stent style anchor.

Figure 23A:
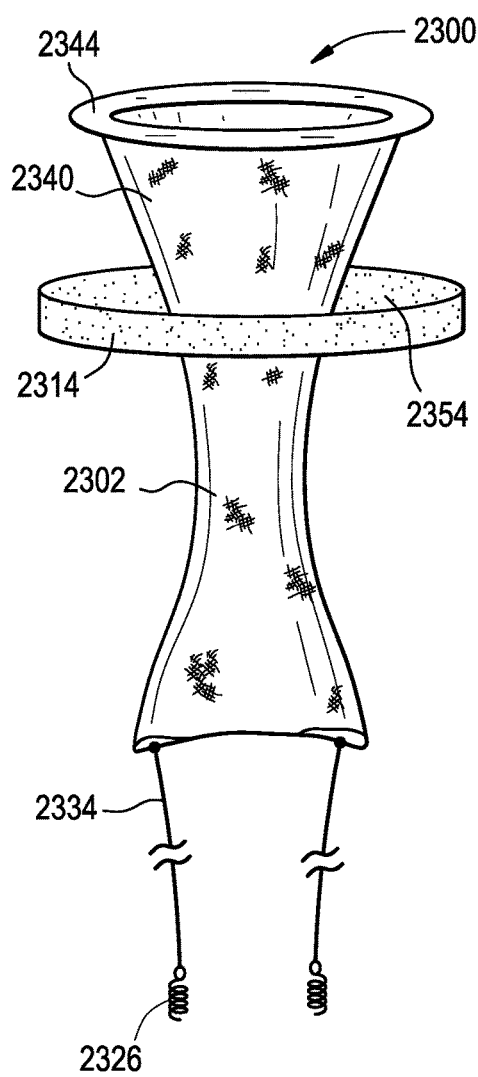
Figure 23B:
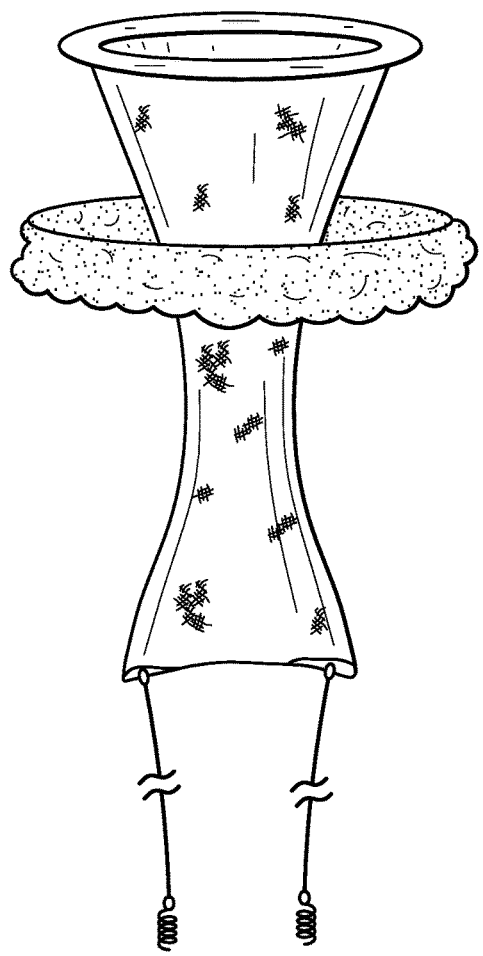

FIGS. 23(a) and 23(b) are illustrations of another embodiment of the present device and shows in sequence an inflatable (or swellable)-mounting feature whereby a cable-style (toroidal) collar is attached to an hourglass shaped cylinder that has an uninflated or undeveloped top-stent attached to the hourglass shaped cylinder. FIG. 23(b) shows whereby the top-stent with polymer matrix absorbs liquid and expands, and thereby operates to seal and mount the device within a native annulus. FIGS. 23(a) and (b) show a two tether embodiment and, e.g. a tissue anchor.

FIGS. 24(a) and 24(b) are illustrations of another embodiment of the present device and show in sequence a thick walled cylinder being compressed by external pressure and closing the channel. FIGS. 24(a) and (b) show a two tether embodiment and a low-aspect bottom-stent style anchor.

FIG. 25(a)-(c) is an illustration of a multiple components on one embodiment of the present invention. FIG. 25(a) shows a cross-section of an open channel having two-tethers. FIG. 25(b) shows a cross-section of a compressed cylinder and closed channel having two tethers. FIG. 25(c) shows an embodiment of the prosthetic medical device having a top stent attached to a collapsible cylinder, the top stent having two contralateral annular anchors, and a two tether embodiment and a low-aspect bottom-stent style anchor.

Figure 26:
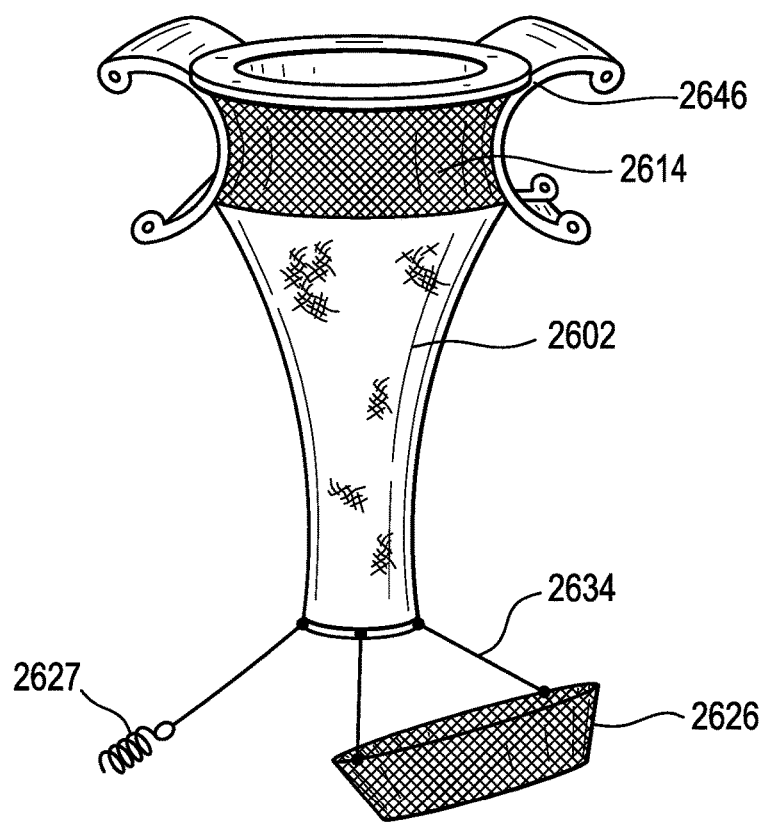

FIG. 26 shows an embodiment of the prosthetic medical device having a top stent attached to a conic cylinder, the top stent having two contralateral annular anchors, and a three tether embodiment with two tethers attached to a low-aspect bottom-stent style anchor, and one tether attached to a tissue anchor.

FIG. 27 is an illustration of another embodiment of the present device and shows a cable-style (toroidal) collar attached to an hourglass shaped closed-bottom perforated cylinder (round perforations) that has a wide-aspect top stent mounted around the cylinder. FIG. 27 shows a two tether embodiment and a low-aspect bottom-stent style anchor.

FIG. 28 is an illustration of another embodiment of the present device and shows a cable-style (toroidal) collar attached to an hourglass shaped closed-bottom perforated cylinder (window-pane perforations) that has a wide-aspect top stent mounted around the cylinder. FIG. 28 shows a two tether embodiment and a low-aspect bottom-stent style anchor.

Figure 29A:
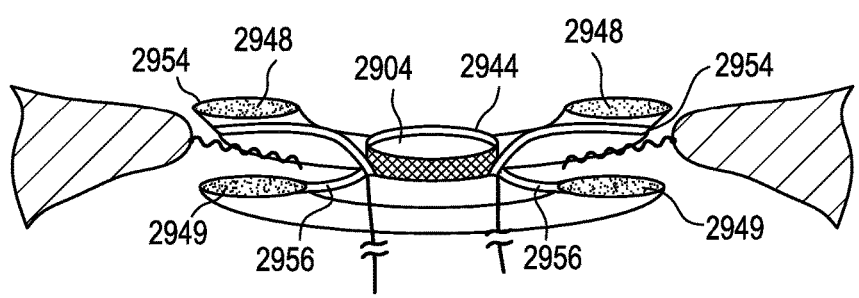
Figure 29B:
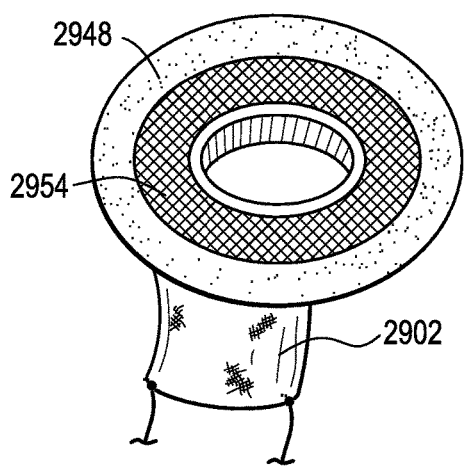
Figure 29C:
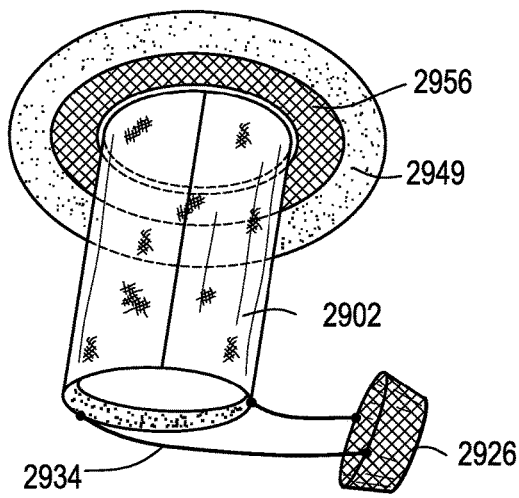
Figure 29D:
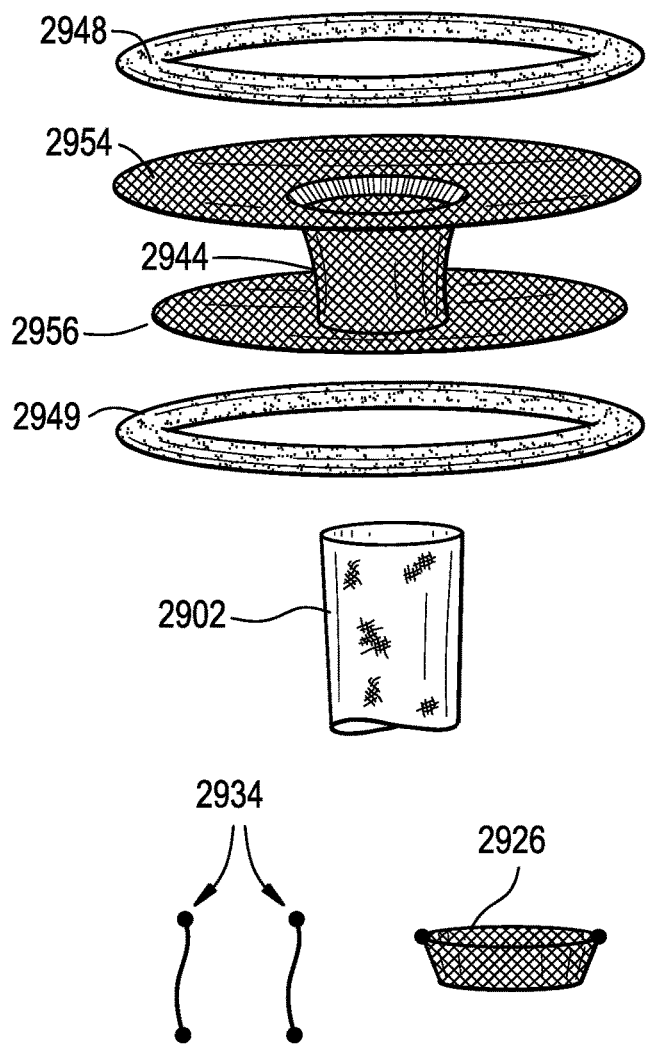

FIGS. 29(a), 29(b), 29(c) and 29(d) are illustrations of another embodiment of the present device and shows a central stent hub with aperture and having a top (apical) circumferential flange and a bottom (ventricular) circumferential flange connected to the hub, with a top toroidal inflatable ring attached to the top (apical) circumferential flange and a bottom toroidal inflatable ring attached to the bottom (ventricular) circumferential flange. FIG. 29(a) is a cross-sectional side view. FIG. 29(b) is a perspective top view. FIG. 29(c) is a perspective bottom view. FIG. 29(d) is an exploded view.

Figure 30A:
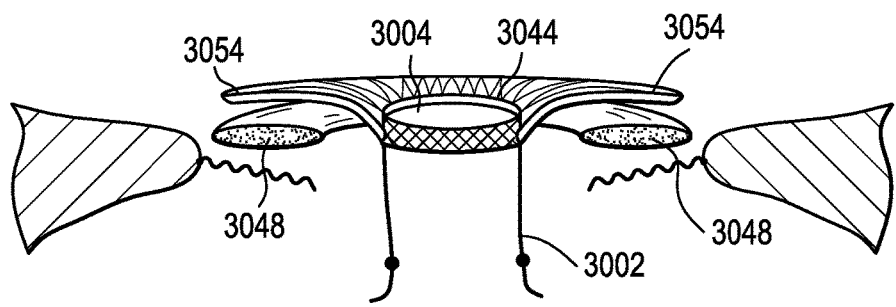
Figure 30B:
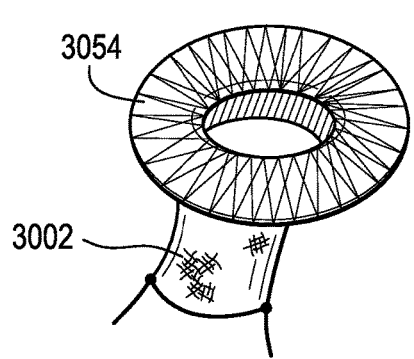
Figure 30C:
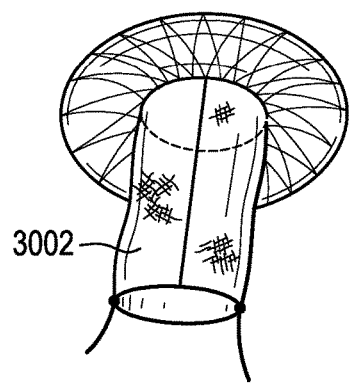
Figure 30D:
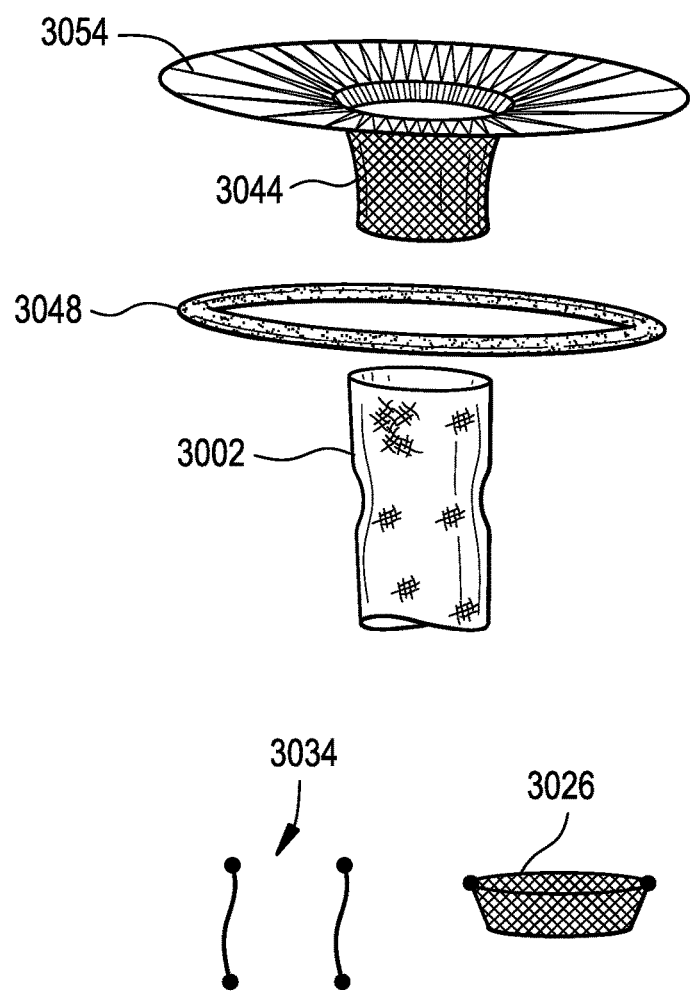

FIGS. 30(a), 30(b), 30(c), and 30(d) are illustrations of another embodiment of the present device and shows a central stent hub with aperture and having a top (apical) circumferential flange connected to the hub, with a top toroidal inflatable ring attached to the top (apical) circumferential flange. FIG. 30(a) is a cross-sectional side view. FIG. 30(b) is a perspective top view. FIG. 30(c) is a perspective bottom view. FIG. 30(d) is an exploded view.

Figure 31:
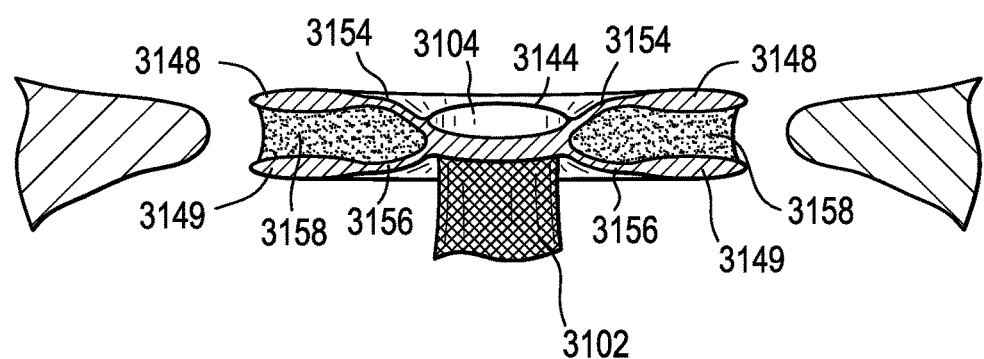

FIG. 31 is a cross-sectional side view of an illustration of another embodiment of the present device and shows a central stent hub with aperture and having a top (apical) circumferential flange and a bottom (ventricular) circumferential flange connected to the hub, with a top toroidal inflatable ring attached to the top (apical) circumferential flange and a bottom toroidal inflatable ring attached to the bottom (ventricular) circumferential flange, and a vacuum compartment between the top and bottom flanges.

Figure 32:
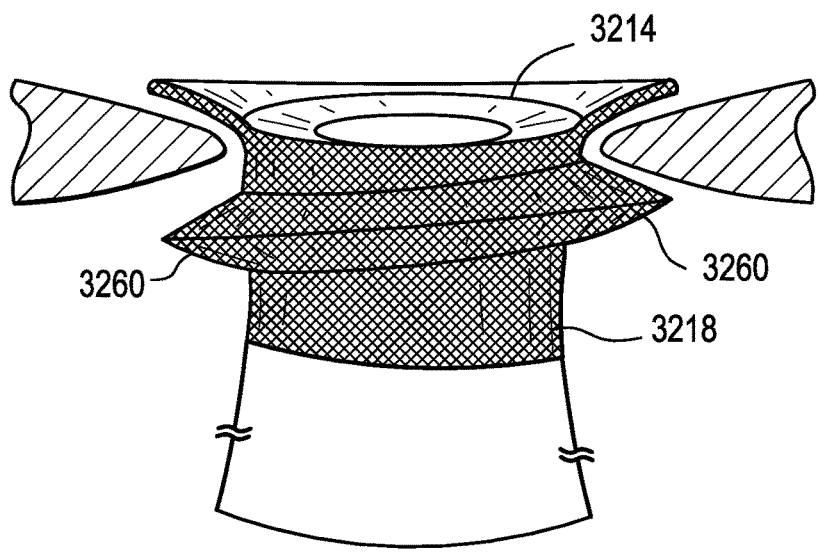

FIG. 32 is an illustration of another embodiment of the present device and shows a stent having a single threaded angled edge structure on the exterior shank surface of the stent.

Figure 33:
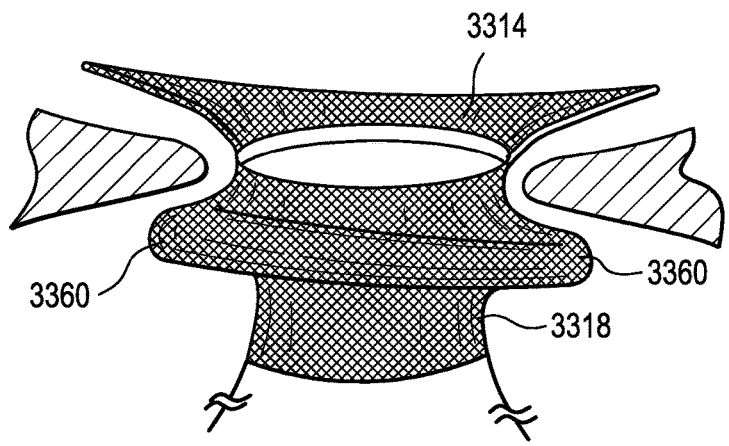

FIG. 33 is an illustration of another embodiment of the present device and shows a stent having a single threaded rounded edge structure on the exterior shank surface of the stent.

Figure 34:
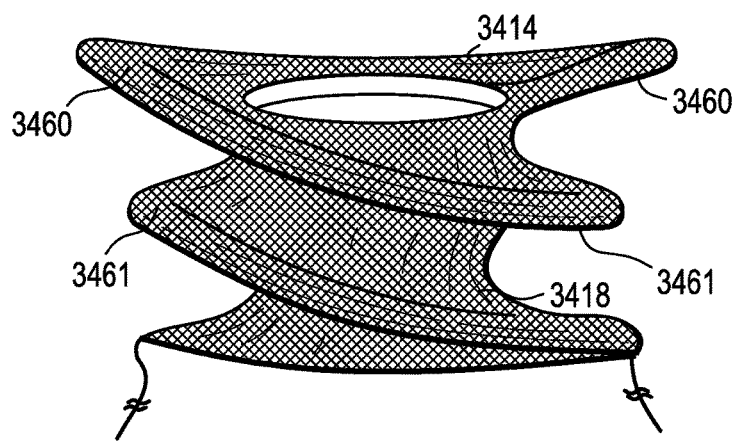

FIG. 34 is an illustration of another embodiment of the present device and shows a stent having a two rounded edge thread structures on the exterior shank surface of the stent.

Figure 35:
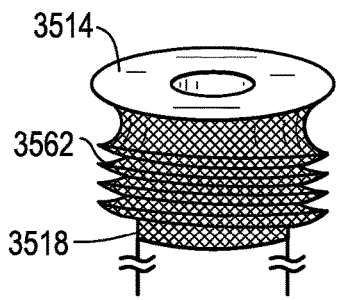

FIG. 35 is an illustration of another embodiment of the present device and shows a stent having a four-thread angled edge structure on the exterior shank surface of the stent.

Figure 36:
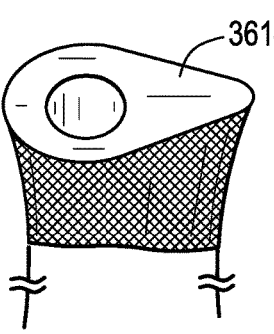

FIG. 36 is an illustration of another embodiment of the present device and shows an offset pear-shape stent structure.

Figure 37:
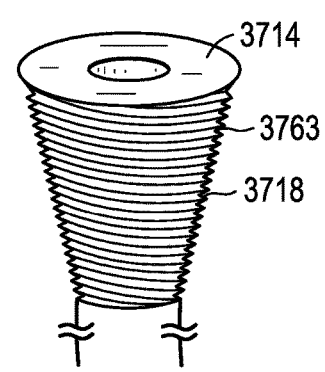
Figure 38A:
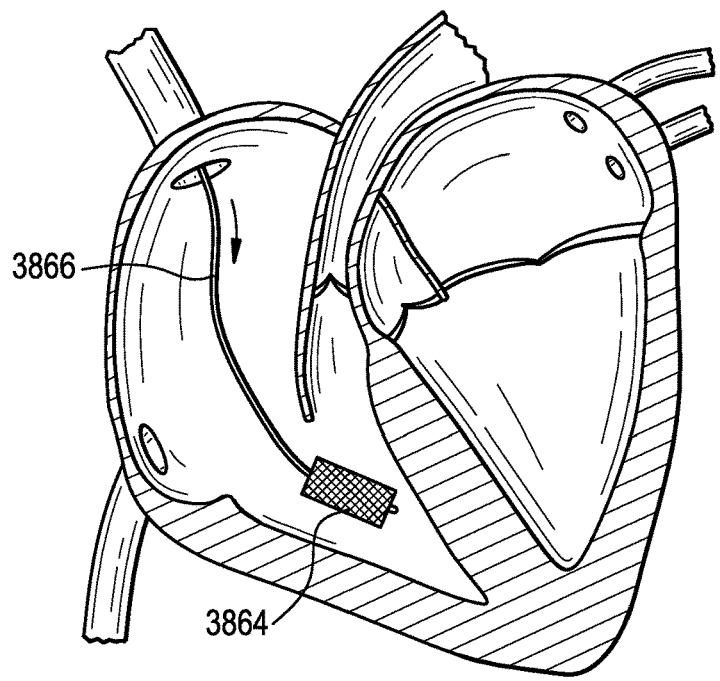
Figure 38B:
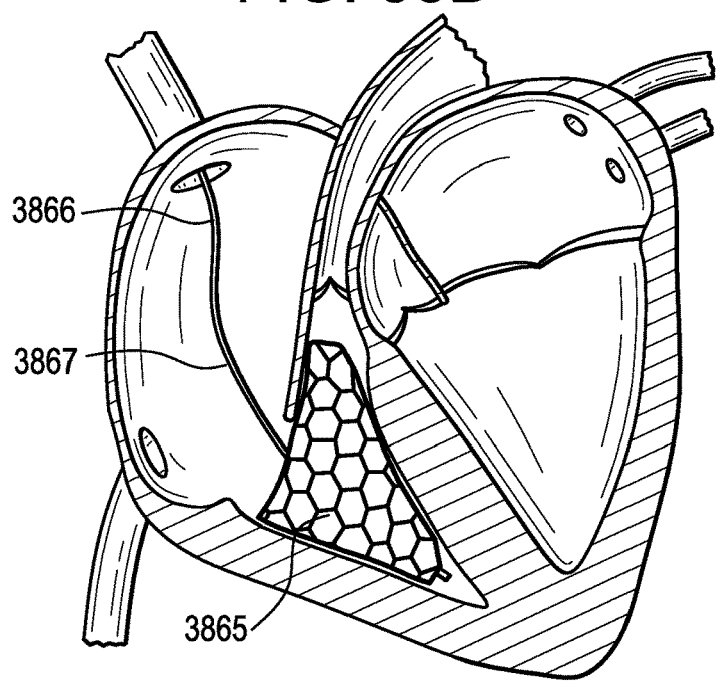
Figure 38C:
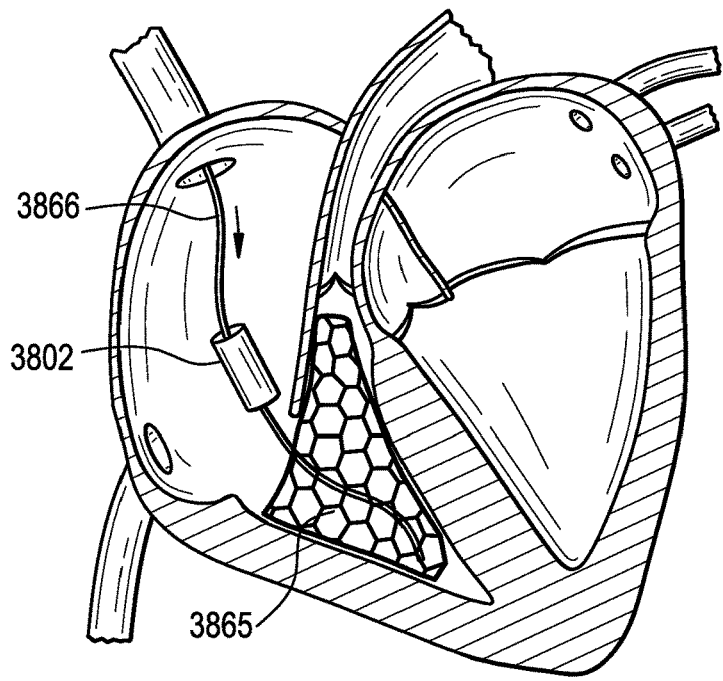
Figure 38D:
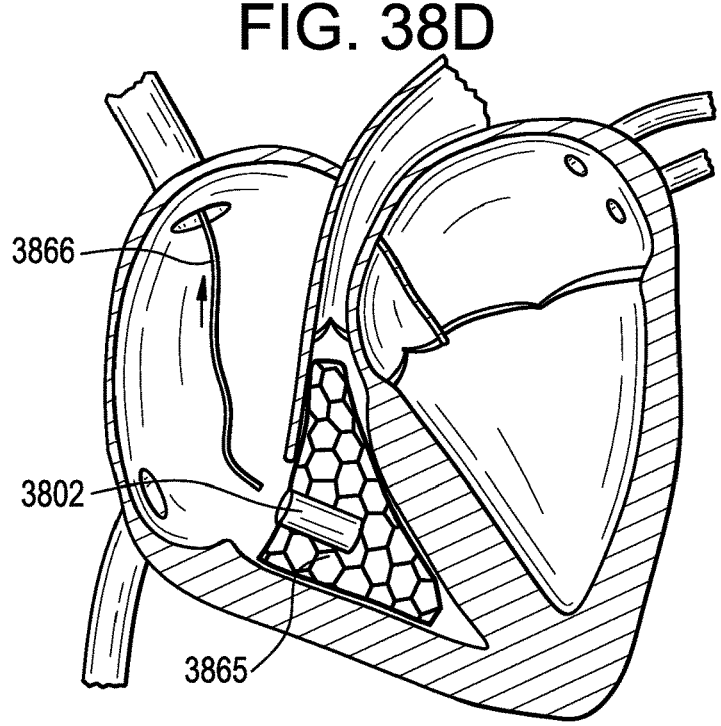

FIG. 37 is an illustration of another embodiment of the present device and shows an elongated tapered stent having threading down the entire outer surface of the stent.

FIG. 38 (a)-(b)-(c)-(d) are illustrations showing in four steps deployment of a passive assist cage having a pliant tubular conduit disposed within. FIG. 38(a) shows catheter delivery of a compressed passive assist cage device to the right ventricle. FIG. 38(b) shows balloon expansion of the passive cage device. FIG. 38(c) shows over-catheter delivery of a pliant tubular conduit into the interior cavity of the passive assist cage device. FIG. 38(d) shows mounting of the conduit within the interior cavity of the passive assist cage and withdrawal of the catheter from the patient.

Figure 39:
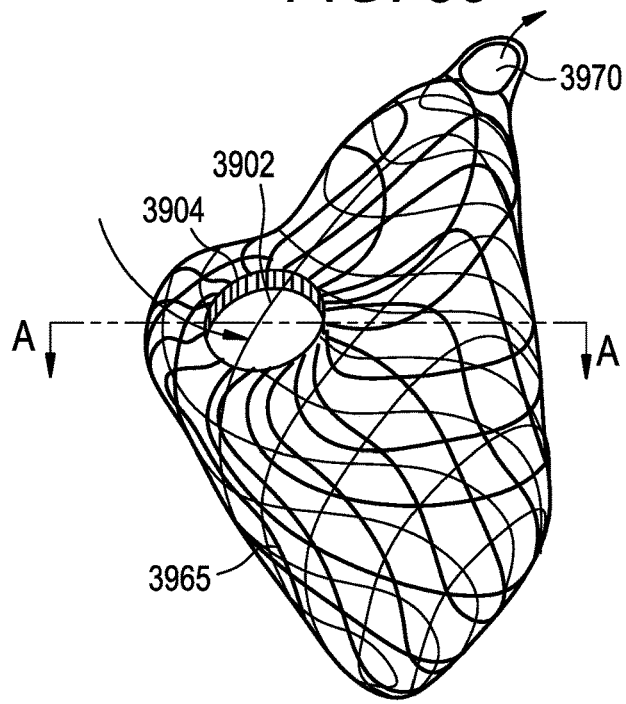

FIG. 39 is an illustration of a three-dimensional volumetric representation of a passive assist cage device.

Figure 40:
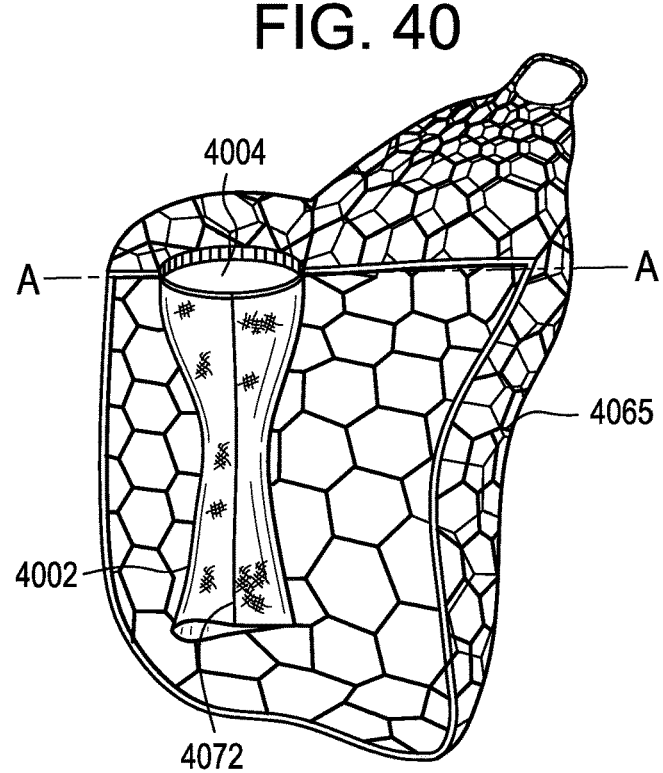

FIG. 40 is an illustration of a three-dimensional volumetric representation of a passive assist cage device with cross-sectional representation along line A-A.

Figure 41:
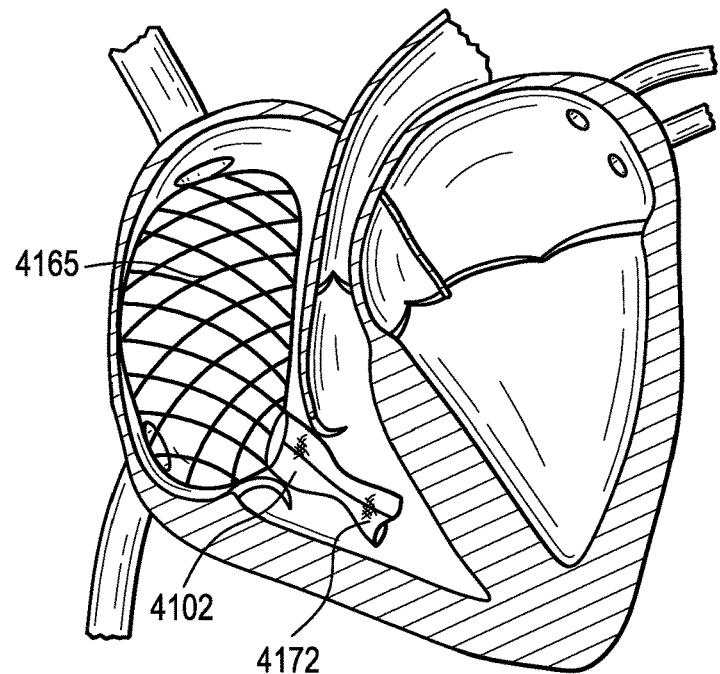

FIG. 41 is an illustration of a passive assist cage device deployed in the right atrium with pliant tubular conduit extending through the tricuspid valve annulus into the right ventricle.

Figure 42:
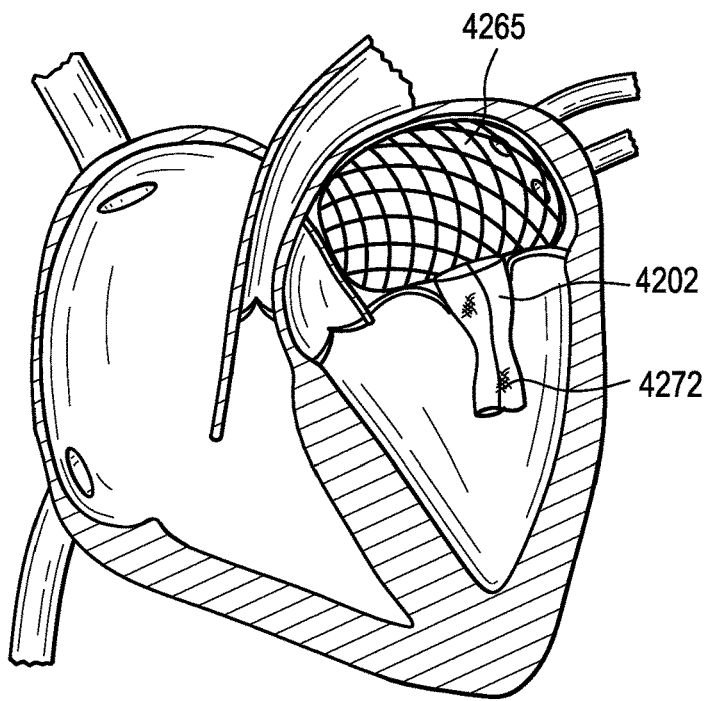

FIG. 42 is an illustration of a passive assist cage device deployed in the left atrium with pliant tubular conduit extending through the mitral valve annulus into the left ventricle.

Figure 43:
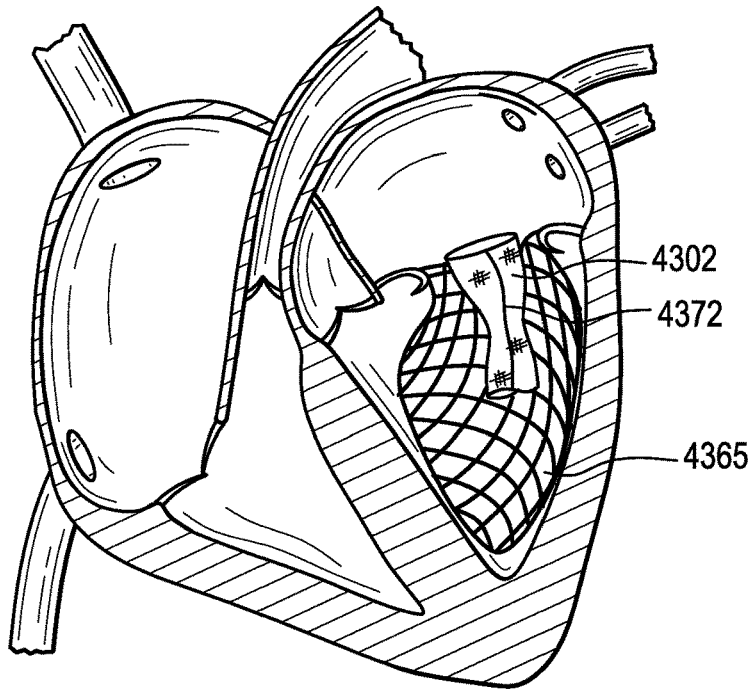

FIG. 43 is an illustration of a passive assist cage device deployed within the left ventricle with pliant tubular conduit disposed within the open cavity of the cage and extending from the mitral valve annulus into the left ventricle.

Figure 44:
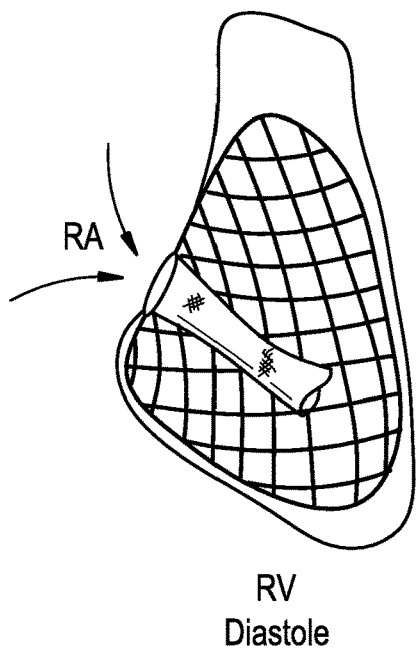

FIG. 44 is an illustration of a passive assist cage device deployed within the right ventricle with pliant tubular conduit in an open position, during diastole, and disposed within the open cavity of the uncompressed cage and extending from the tricuspid valve annulus into the right ventricle.

Figure 45:
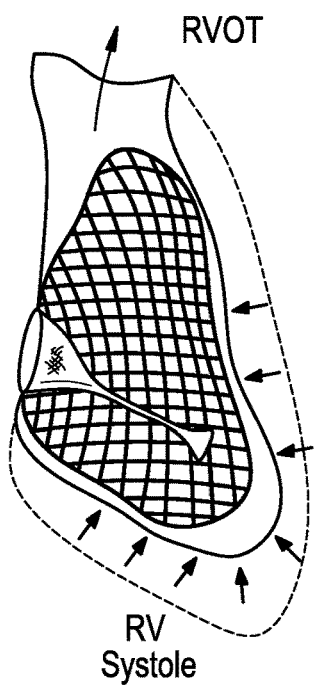

FIG. 45 is an illustration of a passive assist cage device deployed within the right ventricle with pliant tubular conduit in a closed position, during systole, and disposed within the open cavity of the compressed cage and extending from the tricuspid valve annulus into the right ventricle.

Figure 46:
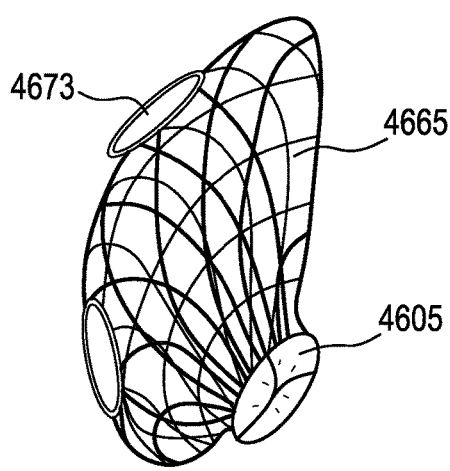

FIG. 46 is an illustration of a passive assist cage configured for deployment within the right atrium, with a prosthetic valve attached to the passive assist cage proximate to the native tricuspid valve, and with optional vascular inlet ports for alignment with the superior and inferior vena cava.

Figure 47:
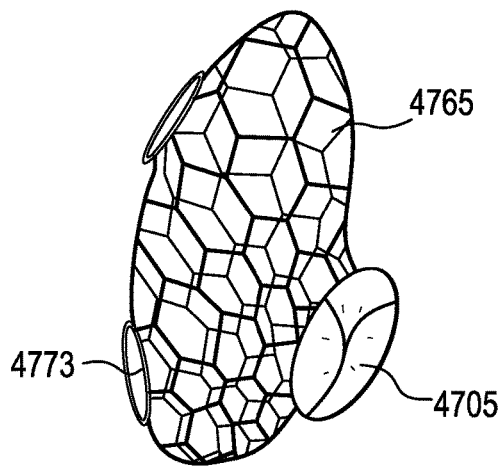

FIG. 47 is an illustration of another embodiment of a passive assist cage configured for deployment within the right atrium, with a large prosthetic valve attached to the passive assist cage proximate to the native tricuspid valve, and with optional vascular inlet ports for alignment with the superior and inferior vena cava.

Figure 48:
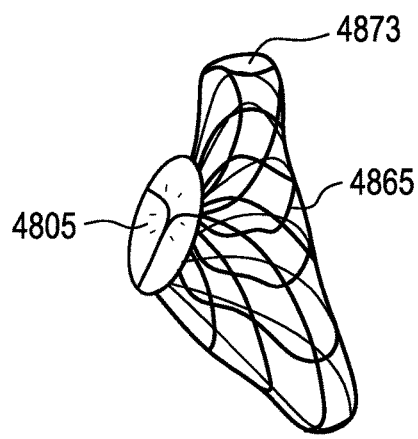

FIG. 48 is an illustration of a passive assist cage configured for deployment within the right ventricle, with a prosthetic valve attached to the passive assist cage proximate to the native tricuspid valve, and with optional vascular outlet ports for alignment with the right ventricular outflow tract.

Figure 49:
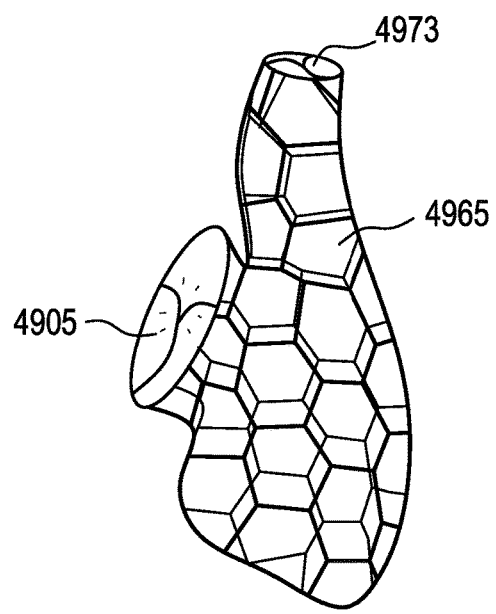

FIG. 49 is an illustration of another embodiment of a passive assist cage configured for deployment within the right ventricle, with a large prosthetic valve attached to the passive assist cage proximate to the native tricuspid valve, and with optional vascular outlet ports for alignment with the right ventricular outflow tract.

Figure 50:
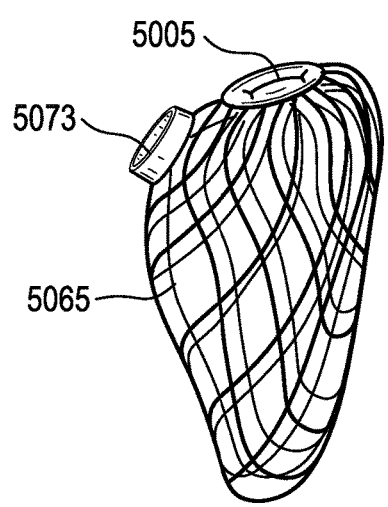

FIG. 50 is an illustration of a passive assist cage configured for deployment within the left ventricle, with a prosthetic valve attached to the passive assist cage proximate to the native mitral valve, and with optional vascular outlet ports for alignment with the left ventricular outflow tract.

Figure 51:
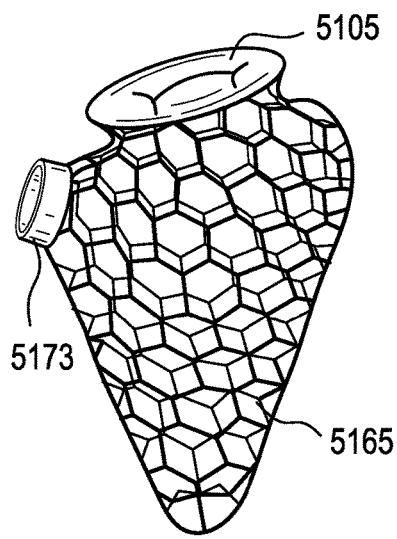

FIG. 51 is an illustration of another embodiment of a passive assist cage configured for deployment within the left ventricle, with a large prosthetic valve attached to the passive assist cage proximate to the native mitral valve, and with optional vascular outlet ports for alignment with the left ventricular outflow tract.

Figure 52:
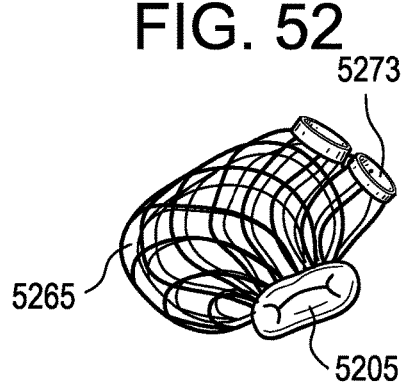

FIG. 52 is an illustration of a passive assist cage configured for deployment within the left atrium, with a prosthetic valve attached to the passive assist cage proximate to the native mitral valve, and with optional vascular inlet ports for alignment with the pulmonary veins.

Figure 53:
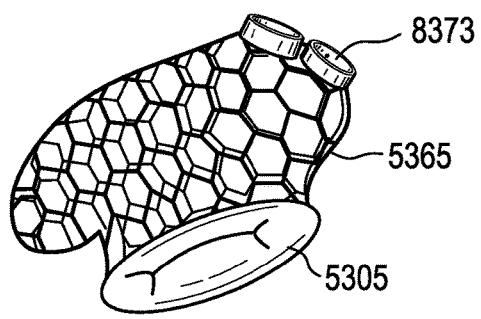

FIG. 53 is an illustration of another embodiment of a passive assist cage configured for deployment within the left atrium, with a large prosthetic valve attached to the passive assist cage proximate to the native mitral valve, and with optional vascular inlet ports for alignment with the pulmonary veins.

DETAILED DESCRIPTION OF THE INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

Bore—The inside diameter of the cylinder tube.
Bypass—A secondary passage for fluid flow.
Discharge hose, or discharge tubing—also called a backwash hose, lay-flat hose. A flexible cylinder or tubing that expands to cylindrical shape (rounded cross-section) due to internal hydraulic pressure when filled with fluid, and that collapses or flattens or seals when the internal hydraulic pressure is reduced by removing or lessening the amount of fluid.

Displacement—The volume of fluid displaced by one complete stroke or revolution

Ejection fraction is a measurement of the percentage of blood leaving your heart each time it contracts. During each heartbeat pumping cycle, the heart contracts and relaxes. When your heart contracts, it ejects blood from the two pumping chambers (ventricles)

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Force—A push or pull acting upon a body. In a hydraulic cylinder, it is the product of the pressure on the fluid, multiplied by the effective area of the cylinder piston.

Prosthetic Valve

For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Frame—Stent Structure

Preferably, the frame is made from superelastic metal wire, such as Nitinol™ wire or other similarly functioning material. The material may be used for the frame/stent, for the collar, and/or for the apex anchor/bottom stent. It is contemplated as within the scope of the invention to use other shape memory alloys such as Cu—Zn—Al—Ni alloys, Cu—Al—Ni alloys, as well as polymer composites including composites containing carbon nanotubes, carbon fibers, metal fibers, glass fibers, and polymer fibers. It is contemplated that the frame/top stent, collar, and bottom stent may be constructed as a braided stent or as a laser cut stent. Such stents are available from any number of commercial manufacturers, such as Pulse Systems. Laser cut stents are preferably made from Nickel-Titanium (Nitinol™), but also without limitation made from stainless steel, cobalt chromium, titanium, and other functionally equivalent metals and alloys, or Pulse Systems braided stent that is shape-set by heat treating on a fixture or mandrel.

One key aspect of the stent design is that it be compressible and when released have the stated property that it return to its original (uncompressed) shape. This requirement limits the potential material selections to metals and plastics that have shape memory properties. With regards to metals, Nitinol has been found to be especially useful since it can be processed to be austhenitic, martensitic or super elastic. Martensitic and super elastic alloys can be processed to demonstrate the required compression features.

Laser Cut Stent

One possible construction of the stent envisions the laser cutting of a thin, isodiametric Nitinol tube. The laser cuts form regular cutouts in the thin Nitinol tube.

Secondarily the tube is placed on a mold of the desired shape, heated to the Martensitic temperature and quenched. The treatment of the stent in this manner will form a stent or stent/cuff or atrial sealing gasket that has shape memory properties and will readily revert to the memory shape at the calibrated temperature.

Braided Wire Stent

A stent can be constructed utilizing simple braiding techniques. Using a Nitinol wire—for example a 0.012" wire—and a simple braiding fixture, the wire is wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided stent is placed on a shaping fixture and placed in a muffle furnace at a specified temperature to set the stent to the desired shape and to develop the martensitic or super elastic properties desired.

Tethers—The tethers are made from surgical-grade materials such as biocompatible polymer suture material. Non-limiting examples of such material include ultra high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines-Anchors-Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the stent body, pierce, rotate into, and hold annular tissue securely.

Tissue—The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Figure 1:
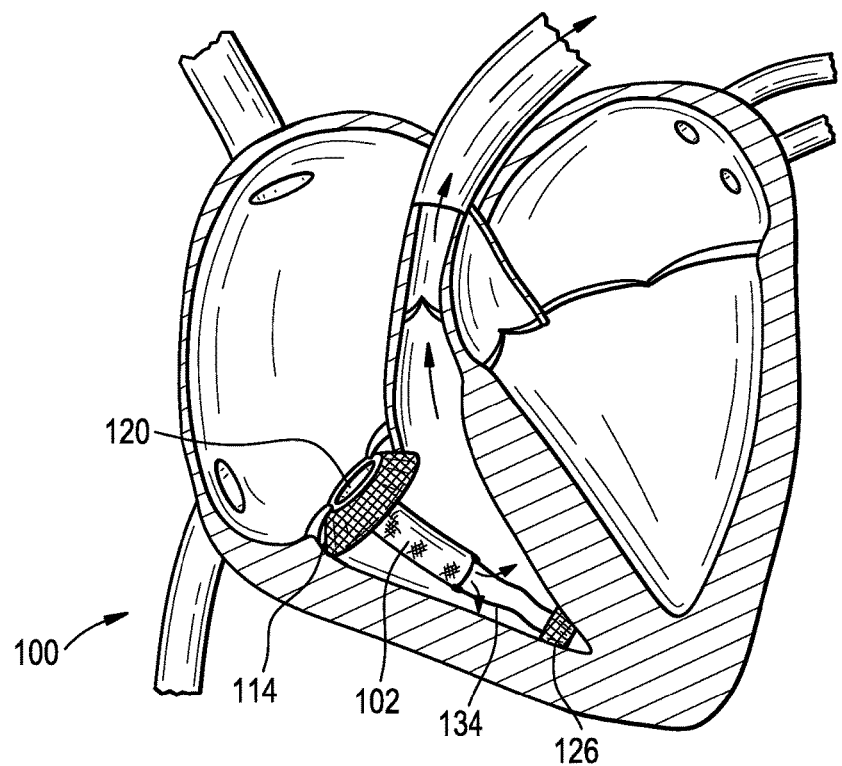
FIG. 1 is an illustration of a cross-section of a heart showing a prosthetic medical device as described and claimed herein deployed in the right ventricle.

Referring now to the drawings, FIG. 1 is an illustration of a cross-section of a heart showing a prosthetic medical device as described and claimed herein deployed in the right ventricle. FIG. 1 shows prosthetic medical device 100 comprised of top stent/resilient subannular frame 114 supporting the elongated flexible cylinder/pliant tubular conduit 102. Tethers 134 connect conduit 102 to anchor/bottom stent 126. Frame (or stent) 114 is anchored below the native tricuspid valve by one or more suitable anchor devices such as surgical clips, clamps, and so forth. Frame 114 is a self-expanding or balloon expandable structure that holds the device within the native annulus and also prevents the device from being ejected into the right atrium during systole. Frame 114, anchor 126 and tethers 134 may be constructed, in whole or in part, of suitable metal, polymeric, or composite materials including nickel-titanium alloy, cobalt-chromium alloy, high cycle fatigue tolerant polymers including composites containing glass fiber, polymer fiber, carbon fiber, metal fiber, carbon nanotube fiber, and composites containing polymer filler materials.

Figure 2:
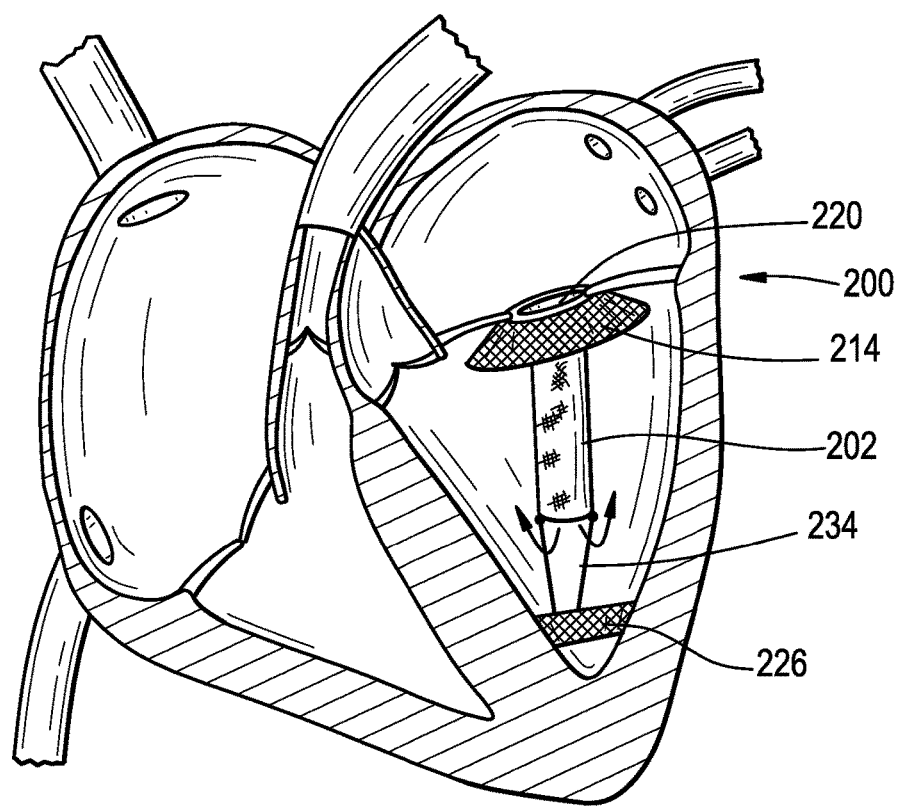
FIG. 2 is an illustration of a cross-section of a heart showing a prosthetic medical device as described and claimed herein deployed in the left ventricle.
Figure 3A:
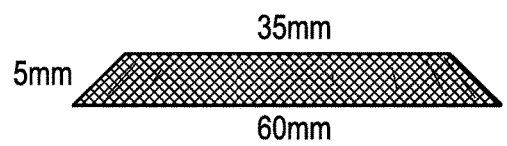
Figure 3B:
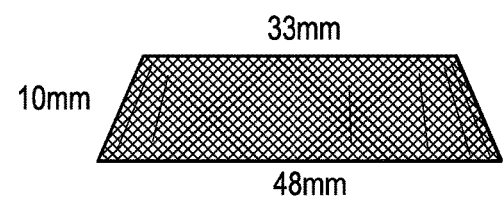
Figure 3C:
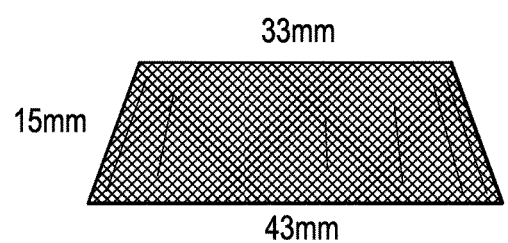
Figure 3D:
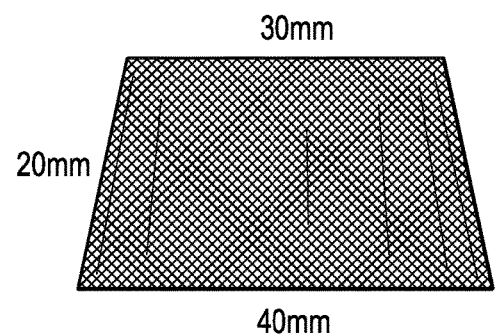
Figure 3E:
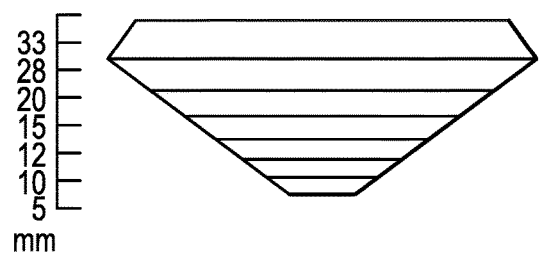
Figure 3M:
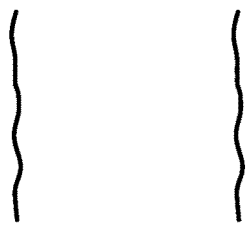
Figure 3N:
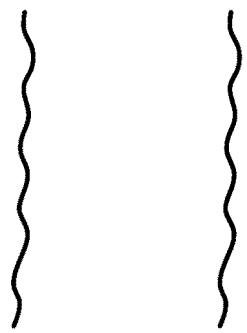
Figure 3O:
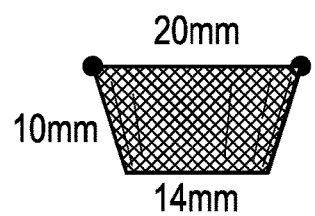
Figure 3P:
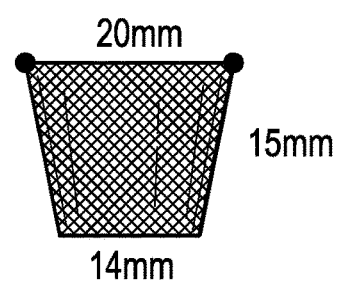
Figure 3Q:
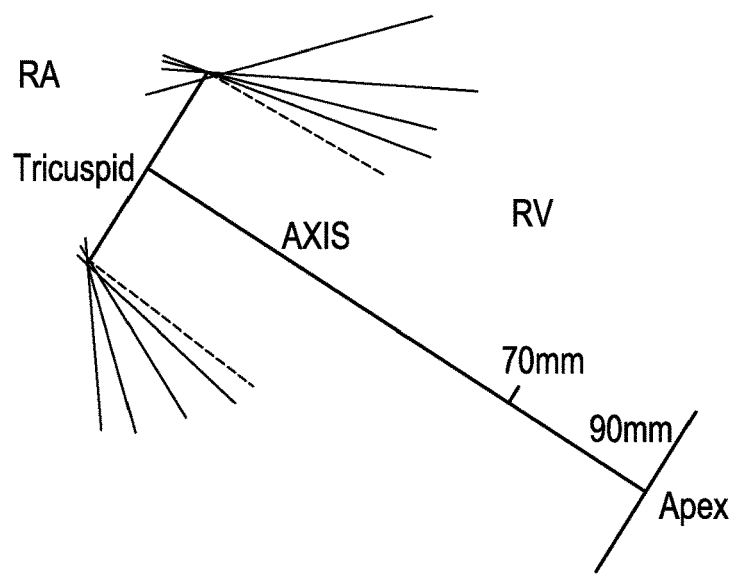
Figure 3R:
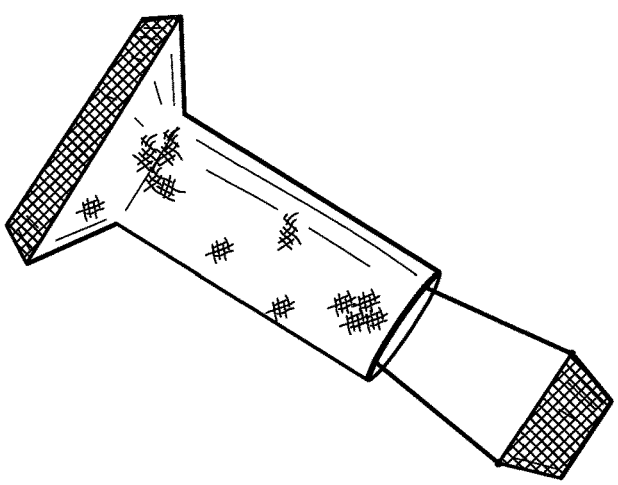

FIG. 2 is an illustration of a cross-section of a heart showing a prosthetic medical device as described and claimed herein deployed in the left ventricle. FIG. 2 shows prosthetic medical device 200 comprised of top stent/resilient subannular frame 214 supporting the elongated flexible cylinder/pliant tubular conduit 202. Tethers 234 connect conduit 202 to anchor/bottom stent 226. Frame (or stent) 214 is anchored below the native mitral valve by one or more suitable anchor devices such as surgical clips, clamps, and so forth. Frame 214 is a self-expanding or balloon expandable structure that holds the device within the native annulus and also prevents the device from being ejected into the right atrium during systole. Frame 214, anchor 226 and tethers 234 may be constructed, in whole or in part, of suitable metal, polymeric, or composite materials including nickel-titanium alloy, cobalt-chromium alloy, high cycle fatigue tolerant polymers including composites containing glass fiber, polymer fiber, carbon fiber, metal fiber, carbon nanotube fiber, and composites containing polymer filler materials.

FIG. 3 is a multi-feature illustration of a various sizes of unassembled top stents, cylinders, tethers, and bottom stents, and also showing a exemplary prosthetic medical device as described and claimed herein. FIG. 3(*a*)-(*d*) are illustrations of top stents, FIG. 3(*e*) is an illustration of a stent cover, FIG. 3(*f*)-(*l*) are illustrations of elongated flexible cylinders, FIG. 3(*m*)-(*n*) are illustrations of bottom stents, FIG. 3(*o*)-(*p*) are illustrations of tethers, FIG. 3(*q*) is a placement schematic for the right atrium and right ventricle and shows the channel axis, and FIG. 3(*r*) is an illustration of exemplary prosthetic medical device as described and claimed herein.

FIGS. 4(*a*) and 4(*b*) are illustrations showing one embodiment of the present prosthetic medical device 400 deployed in a cross-sectional representation of a right atrium and right ventricle. FIGS. 4(*a*) and (*b*) show a time sequence of a funnel-shaped intra-ventricular cylinder/conduit 402 being compressed by systolic action of the right ventricle on the intraventricular blood. FIG. 4 shows funnel shaped conduit 402 mounted to supra-annular collar 444 with collar aperture 420 leading down the conduit lumen to tether 434 connected to apical anchor 426.

FIGS. 5(a) and 5(b) are illustrations showing one embodiment of the present prosthetic medical device 500 deployed in a cross-sectional representation of a right atrium and right ventricle. FIGS. 5(a) and (b) show a time sequence of a conic-shaped intra-ventricular cylinder/conduit 502 being compressed by systolic action of the right ventricle on the intraventricular blood. FIG. 5 shows conic cylinder shaped conduit 502 mounted to supra-annular collar 544 with collar aperture 520 leading down the conduit lumen to tether 534 connected to apical anchor 526.

FIGS. 6(a) and 6(b) are illustrations showing one embodiment of the present prosthetic medical device 600 deployed in a cross-sectional representation of a right atrium and right ventricle. FIGS. 6(a) and (b) show a time sequence of a funnel-shaped intra-ventricular cylinder/conduit 602 being compressed by systolic action of the right ventricle on the intraventricular blood. FIGS. 6(a) and (b) also show an example of a device having a partial atrial collar. FIG. 6 shows wide-funnel shaped conduit 602 mounted to sub-annular collar 614 and supra-annular collar 644 with collar aperture 620 leading down the conduit lumen to tether 634 connected to apical anchor 626. Partial atrial collar panel 650 is shown connected to supra-annular collar 644 and provides additional commissural or other leaflet related sealing to reduce regurgitation.

FIGS. 7(a) and 7(b) are illustrations showing one embodiment of the present prosthetic medical device 700 deployed in a cross-sectional representation of a left atrium and left ventricle. FIGS. 7(a) and (b) show a time sequence of a conic-shaped intra-ventricular cylinder/conduit 702 being compressed by systolic action of the left ventricle on the intraventricular blood. FIGS. 7(a) and 7(b) also illustrate a device having a larger panel-shaped atrial collar 750. FIG. 7 shows conic-cylinder shaped conduit 702 mounted to sub-annular collar 714 and supra-annular collar 744 with collar aperture 720 leading down the conduit lumen to tether 734 connected to apical anchor 726. Panel-shaped atrial collar panel 750 is shown connected to supra-annular collar 744 and provides additional commissural or other leaflet related sealing to reduce regurgitation.

FIG. 8 is a mid-height horizontal cross-sectional illustration of a heart and shows a top atrial view of a collared embodiment of the present invention 800 having three wide-variety leaflet-collar anchors 846. FIG. 8 shows collar 844 having leaflet-collar anchors 846 supporting the pliant tubular conduit 802. FIG. 8 also shows internal surface 810 of the conduit 802.

FIGS. 9(a) and 9(b) are illustrations showing one embodiment of the present prosthetic medical device 900 deployed in a cross-sectional representation of a right atrium and right ventricle. FIGS. 9(a) and (b) show a time sequence of an intra-ventricular cylinder/conduit 902 being compressed by systolic action of the right ventricle on the intraventricular blood. FIGS. 9(a) and (b) also illustrate perivalvular leaflet anchors 952 at the septal and anterior positions that extend from atrium to ventricle. FIG. 9 shows supra-annular collar 944 and sub-annular stent/frame 914 sandwiching the top spacer segment 940 of the conduit/cylinder 902, and providing a spindle-type (disc-spacer-disc) annular anchor to mount the device 900 within the annulus. Tethers 934 anchor the bottom end 908 of conduit 902 to the non-ventricular-wall-perforating apex anchor 926.

FIG. 10 is a mid-height horizontal cross-sectional illustration of a heart and shows a top atrial view of a collared embodiment of the present invention 1000 having nine medium-wide-variety leaflet-collar anchors 1046. FIG. 10 shows collar 1044 having leaflet-collar anchors 1046 supporting the pliant tubular conduit 1002. FIG. 10 also shows internal surface 1010 of the conduit 1002. FIG. 10 also shows aperture 1020 as an alternate embodiment to the circular aperture.

FIGS. 11(a) and 11(b) are illustrations showing one embodiment of the present prosthetic medical device 1100 deployed in a cross-sectional representation of a right atrium and right ventricle. FIGS. 11(a) and (b) show a time sequence of an intra-ventricular cylinder/conduit 1102 being compressed by systolic action of the right ventricle on the intraventricular blood. FIGS. 11(a) and (b) also illustrate perivalvular leaflet anchors 1152 at the septal and anterior positions that extend from atrium to ventricle. FIG. 11 shows supra-annular collar 1144 and sub-annular stent/frame 1114 sandwiching the top spacer segment 1140 of the conduit/cylinder 1102, and providing a spindle-type (disc-spacer-disc) annular anchor to mount the device 1100 within the annulus. Tethers 1134 anchor the bottom end 1108 of conduit 1102 to the non-ventricular-wall-perforating apex anchor 1126.

FIG. 12 is a graphic representation of the change in right ventricular pressure from diastole to systole to diastole. FIG. 12 shows the change in cross-sectional shape of the cylinder when a 2-, 3-, or 4-tether embodiment is deployed. FIG. 12 shows pressure in mm Hg along the Y-axis and the phase of the heart cycle along the X-axis. For the right ventricle, diastole can be, for example, about 5 mm Hg. However, during right ventricular systole, the intraventicular pressure can rise to around 30 mm Hg., closing the conduit. FIG. 12 shows how in a two-tether embodiment, the conduit collapses to form a horizontal bi-fold seal. FIG. 12 shows how in a three-tether embodiment, the conduit collapses to form a triangular tri-fold seal. FIG. 12 also shows how in a four-tether embodiment, the conduit collapses to form a cross-shaped four-fold seal.

FIG. 13 is a graphic representation of the change in left ventricular pressure from diastole to systole to diastole. FIG. 13 shows the change in cross-sectional shape of the cylinder when a 2-, 3-, or 4-tether embodiment is deployed. FIG. 13 shows pressure in mm Hg along the Y-axis and the phase of the heart cycle along the X-axis. For the left ventricle, diastole can be, for example, as low as 8 mm Hg. However, during left ventricular systole, the intraventicular pressure can rise up to 160 mm Hg. or higher, closing the conduit. FIG. 13 shows how in a two-tether embodiment, the conduit collapses to form a horizontal bi-fold seal. FIG. 13 shows how in a three-tether embodiment, the conduit collapses to form a triangular tri-fold seal. FIG. 13 also shows how in a four-tether embodiment, the conduit collapses to form a cross-shaped four-fold seal.

FIGS. 14(a) and 14(b) are illustrations showing one embodiment of the present prosthetic medical device 1400. FIGS. 14(a) and (b) show a time sequence of an intra-ventricular cylinder/conduit 1402 being compressed by hydro- or hemo-dynamic action of tissue that define a pressure cavity on the intracavity fluid. FIGS. 14(a) and (b) also illustrate a simple device having only a frame/stent 1414 and cylinder/conduit 1402 having two tethers 1434 attached to tissue anchors 1426.

FIG. 15(a)-(d) is a multi-component view of an illustration of an hourglass-shaped, three-tether 1534, cable-type (toroid or piped-ring) top stent 1514 embodiment of the present invention 1500. FIG. 15(*a*) shows an illustration of an entire device. FIG. 15(*b*) shows a cross-sectional view of just the frame 1514 and conduit 1502 along line C-C and shows internal surface 1510 of conduit. FIG. 15(*c*) shows a bottom view along line B-B and shows how the cylinder/conduit 1502 collapses to a closed position. FIG. 15(*d*) shows a top view along line A-A looking down the interior of the channel 1504. FIG. 15 also shows bottom stent/anchor 1526.

FIG. 16(*a*)-(*c*) is a multi-component view of an illustration of an hourglass-shaped, two-tether 1634, cable-type (toroid) top stent 1614 embodiment of the present invention. FIG. 16(*a*) shows an illustration of an entire device 1600. FIG. 16(*b*) shows a bottom view along line B-B and shows how the cylinder 1602 collapses to a closed position. FIG. 16(*c*) shows a top view along line A-A looking down the interior of the channel 1604. FIG. 16 also shows bottom stent/anchor 1626.

FIG. 17 is an illustration of another embodiment of the present device 1700 and shows a cable-style (toroidal) collar 1744 attached to an hourglass shaped cylinder/conduit 1702 that has a wide-aspect top stent/frame 1714 mounted around the cylinder 1702. FIG. 17 shows a two tether 1734 embodiment and a low-aspect bottom-stent style anchor 1726.

FIG. 18 is an illustration of another embodiment of the present device 1800 and shows a cable-style (toroidal) collar 1844 with a large panel 1850 attached to an hourglass shaped conduit/cylinder 1802 that has a narrow-aspect top stent/frame 1814 mounted around the cylinder 1802. FIG. 18 shows a two tether 1834 embodiment and a narrow-aspect bottom-stent style anchor 1826.

FIG. 19 is an illustration of another embodiment of the present device 1900 and shows a cable-style (toroidal) collar 1944 with a large panel 1950 attached to an hourglass shaped conduit 1902 but does not have any top stent mounted around the cylinder/conduit 1902. FIG. 19 shows a two tether 1934 embodiment and a low-aspect bottom-stent style anchor 1926.

FIG. 20 is an illustration of another embodiment of the present device 2000 and shows a cable-style (toroidal) collar 2044 with a large panel 2050 attached to an hourglass shaped cylinder 2002 and has a covered-frame style top stent 2014 mounted around the cylinder/conduit 2002. FIG. 20 shows a two tether 2034 embodiment and a low-aspect bottom-stent style anchor 2026.

FIGS. 21(*a*) and 21(*b*) is an illustration of another embodiment of the present device 2100 and shows a vacuum-mounting feature. FIGS. 21(*a*) and (*b*) show a time-sequence of the deflation of a filled compartment. FIGS. 21(*a*) and (*b*) show an embodiment whereby a cable-style (toroidal) collar 2144 is attached to an hourglass shaped cylinder 2102 (conduit) that has a covered-frame style top stent 2114 mounted around the cylinder 2102, but where the top stent 2114 has a covered nitinol frame that supports a deflatable ring 2148, wherein the deflatable ring 2148 is comprised of a toroid-shaped sealed compartment 2147 (within cover) having a valve 2149, said sealed compartment 2147 fillable with a biocompatible liquid or gas, wherein upon removal of some or all of the biocompatible liquid or gas, the deflatable ring 2148 works in cooperation with the (non-moving) collar 2144 to compress the top spacer segment 2140 of the cylinder to a reduced height and thereby operate to seal and mount the device within a native annulus. FIGS. 21(*a*) and (*b*) shows a two tether 2134 embodiment and a low-aspect bottom-stent style anchor 2126. FIG. 21(*c*) shows a cross-sectional view, sans cover.

FIGS. 22(*a*) and 22(*b*) are illustrations of another embodiment of the present device 2200 and shows in sequence an expansion-mounting feature whereby a compressed top-stent 2214 is attached to an hourglass shaped cylinder 2202 but whereby the top-stent 2214 and the bottom stent 2226 are comprised of a compressed material that is released, or of an inelastic deformable material, and thereby operate to seal and mount the device within a native annulus and native mount-area. FIG. 22 shows a two tether 2234 embodiment and a low-aspect bottom-stent style anchor 2226.

FIGS. 23(*a*) and 23(*b*) are illustrations of another embodiment of the present device 2300 and shows in sequence an inflatable (or swellable)-mounting feature whereby a cable-style (toroidal) collar 2344 is attached to an hourglass shaped cylinder 2302 that has an uninflated or undeveloped top-stent 2314 attached to the hourglass shaped cylinder 2302. FIG. 23(*b*) shows whereby the top-stent 2314 with polymer matrix 2354 absorbs liquid and expands, and thereby operates to seal and mount the device within a native annulus. FIGS. 23(*a*) and (*b*) show a two tether 2334 embodiment and, e.g. a tissue anchor(s) 2326.

FIGS. 24(*a*) and 24(*b*) are illustrations of another embodiment of the present device and show in sequence a thick walled cylinder 2402 being compressed by external pressure and closing the channel 2404. FIGS. 24(*a*) and (*b*) show a two tether 2434 embodiment and a low-aspect bottom-stent style anchor 2426. FIG. 24 also shows how frame 2414 can be configured to be approximately the same height of the conduit 2402.

FIG. 25(*a*)-(*c*) is an illustration of a multiple components on one embodiment of the present invention. FIG. 25(*a*) shows a cross-section of an open channel having two-tethers. FIG. 25(*b*) shows a cross-section of a compressed cylinder and closed channel having two tethers. FIG. 25(*c*) shows an embodiment of the prosthetic medical device having a top stent 2514 attached to a collapsible cylinder conduit 2502, the top stent 2514 having two contralateral annular anchors 2546, and a two tether 2534 embodiment and a low-aspect bottom-stent style anchor 2526.

FIG. 26 shows an embodiment of the prosthetic medical device having a top stent 2614 attached to a conic cylinder conduit 2602, the top stent 2614 having two contralateral annular anchors 2646, and a three tether 2634 embodiment with two tethers attached to a low-aspect bottom-stent style anchor 2626, and one tether attached to a tissue anchor 2627.

FIG. 27 is an illustration of another embodiment 2700 of the present device and shows a cable-style (toroidal) collar 2744 attached to an hourglass shaped closed-bottom perforated cylinder/conduit 2702 with round perforations 2756 that has a wide-aspect top stent 2714 mounted around the cylinder 2702. FIG. 27 shows a two tether 2734 embodiment and a low-aspect bottom-stent style anchor 2726.

FIG. 28 is an illustration of another embodiment 2800 of the present device and shows a cable-style (toroidal) collar 2844 attached to an hourglass shaped closed-bottom perforated cylinder 2802 with window-pane perforations 2856 and that has a wide-aspect top stent 2814 mounted around the cylinder/conduit 2802. FIG. 28 shows a two tether 2834 embodiment and a low-aspect bottom-stent style anchor 2826.

FIGS. 29(*a*), 29(*b*), 29(*c*) and 29(*d*) are illustrations of another embodiment of the present device and shows a central stent hub 2944 with aperture 2904 and having a top (apical) circumferential flange 2954 and a bottom (ventricular) circumferential flange 2956 connected to the hub 2944, with a top toroidal inflatable ring 2948 attached to the top (apical) circumferential flange 2954 and a bottom toroidal inflatable ring 2949 attached to the bottom (ventricular) circumferential flange 2956. FIG. 29(*a*) is a cross-sectional side view and shows how the native leaflet, indicated by wavy line, are compressed and captured within the circumferential channel formed by the top flange, hub wall, and bottom flange. FIG. 29(*b*) is a perspective top view and shows how the top ring 2948 is at the outer circumference of the flange 2954 with a stent top spacer region leading to the aperture annulus. FIG. 29(*c*) is a perspective bottom view and shows how the bottom ring 2949 and bottom spacer region lead to the subannular aperture annulus. In a preferred embodiment, the pliant tubular channel 2902 is attached to the subannular aperture annulus and leads into the ventricle, shown here in outline form to better show the underside of the stent structure. FIG. 29(*c*) shows tethers 2934 connecting bottom anchor unit 2926 to conduit 2902. FIG. 29(*d*) is an exploded view and shows the component parts of one embodiment. Fillable (or filled or compressive matrix) top ring 2948 mounts atop top circumferential flange 2954, and which is in urn connected to central stent hub 2944. Hub 2944 is connected to bottom circumferential flange 2956, and which has bottom ring 2949 disposed on its bottom surface. Pliant tubular conduit 2902 is connected in communication with the central aperture of the hub 2944. Tethers 2934 connect conduit 2902 to bottom anchor/stent 2926.

FIGS. 30(*a*), 30(*b*), 30(*c*) and 30(*d*) are illustrations of another embodiment of the present device and shows a central stent hub 3044 with aperture 3004 and having a top (apical) circumferential flange 3054 connected to the hub 3044, with a top toroidal inflatable ring 3048 attached to the top (apical) circumferential flange 3054. FIG. 30(*a*) is a cross-sectional side view and shows how the native leaflet, indicated by wavy line, sandwiches the ring and forms a seal to prevent regurgitation during systole. FIG. 30(*b*) is a perspective top view and shows how the top surface of the flange may be left as open mesh stent material. FIG. 30(*c*) is a perspective bottom view and shows the native leaflet flattened and compressed by the inflatable ring above it (not seen). FIG. 30(*c*) also shows pliant tubular channel 3002 is attached to the subannular aperture annulus and leading into the ventricle. FIG. 30(*d*) is an exploded view and shows top flange 3054 connected to central hub 3044. Sealing ring 3048 is mounted on the underside of the flange 3054. Conduit 3002 for a channel with and is in communication with the interior channel of hub 3044. tethers 23034 connect conduit to bottom anchor 3026.

FIG. 31 is a cross-sectional side view of an illustration of another embodiment of the present device and shows a central stent hub 3144 with aperture 3104 and having a top (apical) circumferential flange 3154 and a bottom (ventricular) circumferential flange 3156 connected to the hub 3144, with a top toroidal inflatable ring 3148 attached to the top (apical) circumferential flange 3154 and a bottom toroidal inflatable ring 3149 attached to the bottom (ventricular) circumferential flange 3156, and a vacuum compartment 3158 between the top and bottom flanges. FIG. 31 also shows pliant tubular channel 3102 is attached to the subannular aperture annulus and leading into the ventricle.

FIG. 32 is an illustration of another embodiment of the present device and shows a 3214 stent having a single threaded angled edge structure 3260 on the exterior shank surface 3218 of the stent 3214. This angled edge threading allows for a simple circular screw-type deployment of the device into the native annulus to aid in sealing and sizing of the stent frame into the native annulus.

FIG. 33 is an illustration of another embodiment of the present device and shows a stent 3314 having a single threaded rounded edge structure 3360 on the exterior shank surface 3318 of the stent 3314. This rounded edge threading allows for a simple circular screw-type deployment of the device into the native annulus to aid in sealing and sizing of the stent frame into the native annulus.

FIG. 34 is an illustration of another embodiment of the present device and shows a stent 3414 having a first rounded edge thread structure 3460 and a second rounded edge thread structure 3461 on the exterior shank surface 3418 of the stent 3414. This multiple rounded edge threading allows for a simple circular screw-type deployment of the device into the native annulus to aid in sealing and sizing of the stent frame into the native annulus.

FIG. 35 is an illustration of another embodiment of the present device and shows a stent 3514 having a four-thread angled edge structure 3562 on the exterior shank surface 3518 of the stent 3514. This threading allows for a circular screw-type deployment of the device into the native annulus and allows for proper sizing and seating of the stent frame into the native annulus during deployment since pre-operative radiological studies of the size of the native annulus can be inaccurate leading to the improper selection of the correct size of prosthetic stent frame.

FIG. 36 is an illustration of another embodiment of the present device and shows an offset pear-shape stent structure 3614.

FIG. 37 is an illustration of another embodiment of the present device and shows an elongated tapered stent 3714 having threading 3763 down the entire outer surface 3718 of the stent 3714. This threading allows for a circular screw-type deployment of the device into the native annulus and the tapered form of the stent allows for proper sizing of the the stent during deployment since pre-operative radiological studies of the size of the native annulus can be inaccurate leading to the improper selection of the correct size of prosthetic stent frame.

FIG. 38 (*a*)-(*b*)-(*c*)-(*d*) are illustrations showing in four steps deployment of a passive assist cage having a pliant tubular conduit disposed within. FIG. 38(*a*) shows balloon expanding delivery catheter 3866 delivering a compressed, unexpanded passive assist cage device 3864 to the right ventricle. FIG. 38(*b*) shows balloon segment 3867 expansion of the passive cage device 3865. FIG. 38(*c*) shows over-catheter delivery of a pliant tubular conduit 3802 into the interior cavity of the uncompressed, expanded passive assist cage device 3865. FIG. 38(*d*) shows mounting of the conduit 3802 within the interior cavity of the passive assist cage 3865 and withdrawal of the catheter 3866 from the patient.

FIG. 39 is an illustration of a three-dimensional volumetric representation of a braided-stent embodiment of passive assist cage device 3965. Conduit 3902 is shown mounted within the cavity of the passive assist cage 3965 with aperture 3904 leading into the interior channel of the conduit 3902. Passive assist cage 3965 is shown with right ventricular outflow tract (RVOT) outlet 3970 to provide an unobstructed opening for compressed fluid to flow during systolic compression.

FIG. 40 is an illustration of a three-dimensional volumetric representation of a laser-cut passive assist cage device 4065 with cross-sectional representation along line A-A. Aperture 4004 is shown leading to the interior of conduit 4002. Semi-rigid conduit support 4072 is shown attached to or within conduit 4002 to provide a structure to eliminate risk of prolapse of the conduit 4002 during high-pressure compression. In use, during diastole fluid flows unobstructed from the atrium through the conduit 4002 into the ventricle. During compression, systole, the conduit 4002 is configured to collapse along its X-axis, Z-axis, or both (diameter of cylinder is substantially reduced or closed). The conduit 4002 is closed by action of the fluid pressure on its outer surface. The open cavity cage 4065 provides a compressive resistance outward against the inward cardiac ventricular muscle compression. However, during recovery, the open cavity cage 4065 provides an outward spring-like passive assist to the outward moving cardiac ventricular muscle.

FIG. 41 is an illustration of a passive assist cage device deployed in the right atrium with pliant tubular conduit extending through the tricuspid valve annulus into the right ventricle. In this embodiment, semi-rigid conduit support is shown attached to or within conduit.

FIG. 42 is an illustration of a passive assist cage device deployed in the left atrium with pliant tubular conduit extending through the mitral valve annulus into the left ventricle. In this embodiment, semi-rigid conduit support is shown attached to or within conduit.

FIG. 43 is an illustration of a passive assist cage device deployed within the left ventricle with pliant tubular conduit disposed within the open cavity of the cage and extending from the mitral valve annulus into the left ventricle. In this embodiment, semi-rigid conduit support is shown attached to or within conduit.

FIG. 44 is an illustration of a passive assist cage device deployed within the right ventricle with pliant tubular conduit in an open position, during diastole, and disposed within the open cavity of the uncompressed cage and extending from the tricuspid valve annulus into the right ventricle.

FIG. 45 is an illustration of a passive assist cage device deployed within the right ventricle with pliant tubular conduit in a closed position, during systole, and disposed within the open cavity of the compressed cage and extending from the tricuspid valve annulus into the right ventricle.

FIG. 46 is an illustration of a passive assist cage 4665 configured for deployment within the right atrium, with a prosthetic valve 4605 attached to the passive assist cage 4665 proximate to the native tricuspid valve, and with optional vascular inlet ports 4673 for alignment with the superior and inferior vena cava to receive blood entering the right atrium. In use, during diastole, fluid flows unobstructed into the atrium through the inlet ports 4673. During diastole, the prosthetic valve 4605 is open and releases collected fluid into the adjoining right ventricle. During systole, compression, the valve 4605 is closed by action of the fluid pressure on its ventricular surface. The passive assist cage 4665 provides a compressive resistance outward against the inner surface of the right atrium. During recovery, the passive assist cage 4665 provides an outward spring-like passive assist to the outward moving cardiac atrial tissue muscle.

FIG. 47 is an illustration of another embodiment of a passive assist cage configured for deployment within the right atrium, with a large prosthetic valve attached to the passive assist cage proximate to the native tricuspid valve, and with optional vascular inlet ports for alignment with the superior and inferior vena cava. Similar to FIG. 46, in use, during diastole, fluid flows unobstructed into the atrium through the inlet ports 4773. During diastole, the prosthetic valve 4705 is open and releases collected fluid into the adjoining right ventricle. During systole, compression, the valve 4705 is closed by action of the fluid pressure on its ventricular-facing surface. The passive assist cage 4765 provides a compressive resistance outward against the inner surface of the right atrium. During recovery, the passive assist cage 4765 provides an outward spring-like passive assist to the outward moving cardiac atrial tissue muscle.

FIG. 48 is an illustration of a passive assist cage 4865 configured for deployment within the right ventricle, with a prosthetic valve 4805 attached to the passive assist cage 4865 proximate to the native tricuspid valve, and with optional vascular outlet ports 4873 for alignment with the right ventricular outflow tract. In use, during diastole, fluid flows unobstructed into the right ventricle through the prosthetic valve 4805. During diastole, the prosthetic valve 4805 is open and allows collected fluid from the adjoining right atrium into the right ventricle. During systole, compression, the valve 4805 is closed by action of the fluid pressure on its ventricular-facing surface. The passive assist cage 4865 provides a compressive resistance outward against the inner surface of the right ventricle. During recovery, the passive assist cage 4865 provides an outward spring-like passive assist to the outward moving cardiac ventricular muscle.

FIG. 49 is an illustration of another embodiment of a passive assist cage configured for deployment within the right ventricle, with a large prosthetic valve attached to the passive assist cage proximate to the native tricuspid valve, and with optional vascular outlet ports for alignment with the right ventricular outflow tract. Similar to FIG. 48, in use, during diastole, fluid flows unobstructed into the right ventricle through the prosthetic valve 4905. During diastole, the prosthetic valve 4905 is open and allows collected fluid from the adjoining right atrium into the right ventricle. During systole, compression, the valve 4905 is closed by action of the fluid pressure on its ventricular-facing surface. The passive assist cage 4965 provides a compressive resistance outward against the inner surface of the right ventricle. During recovery, the passive assist cage 4965 provides an outward spring-like passive assist to the outward moving cardiac ventricular muscle.

FIG. 50 is an illustration of a passive assist cage 5065 configured for deployment within the left ventricle, with a prosthetic valve 5005 attached to the passive assist cage 5065 proximate to the native mitral valve, and with optional vascular outlet ports 5073 for alignment with the left ventricular outflow tract. In use, during diastole, fluid flows unobstructed into the left ventricle through the prosthetic valve 5005. During diastole, the prosthetic valve 5005 is open and allows collected fluid from the adjoining left atrium into the left ventricle. During systole, compression, the valve 5005 is closed by action of the fluid pressure on its ventricular-facing surface. The passive assist cage 5065 provides a compressive resistance outward against the inner surface of the left ventricle. During recovery, the passive assist cage 5065 provides an outward spring-like passive assist to the outward-moving cardiac ventricular muscle.

FIG. 51 is an illustration of another embodiment of a passive assist cage configured for deployment within the left ventricle, with a large prosthetic valve attached to the passive assist cage proximate to the native mitral valve, and with optional vascular outlet ports for alignment with the left ventricular outflow tract. Similar to FIG. 50, in use, during diastole, fluid flows unobstructed into the left ventricle through the prosthetic valve 5105. During diastole, the prosthetic valve 5105 is open and allows collected fluid from the adjoining left atrium into the left ventricle. During systole, compression, the valve 5105 is closed by action of the fluid pressure on its ventricular-facing surface. The passive assist cage 5165 provides a compressive resistance outward against the inner surface of the left ventricle.

During recovery, the passive assist cage 5165 provides an outward spring-like passive assist to the outward-moving cardiac ventricular muscle.

FIG. 52 is an illustration of a passive assist cage 5265 configured for deployment within the left atrium, with a prosthetic valve 5205 attached to the passive assist cage 5265 proximate to the native mitral valve, and with optional vascular inlet ports 5273 for alignment with the pulmonary veins. In use, during diastole, fluid flows unobstructed into the left atrium through the pulmonary veins. During diastole, the prosthetic valve 5205 is open and allows collected fluid from the left atrium into the left ventricle. During systole, compression, the prosthetic valve 5205 is closed by action of the fluid pressure on its ventricular-facing surface. The passive assist cage 5265 provides a compressive resistance outward against the inner surface of the left atrium. During recovery, the passive assist cage 5265 provides an outward spring-like passive assist to the outward-moving cardiac atrial tissue.

FIG. 53 is an illustration of another embodiment of a passive assist cage 5365 configured for deployment within the left atrium, with a large prosthetic valve 5305 attached to the passive assist cage 5365 proximate to the native mitral valve, and with optional vascular inlet ports 5373 for alignment with the pulmonary veins. Similar to FIG. 52, in use, during diastole, fluid flows unobstructed into the left atrium through the pulmonary veins. During diastole, the prosthetic valve 5305 is open and allows collected fluid from the left atrium into the left ventricle. During systole, compression, the prosthetic valve 5305 is closed by action of the fluid pressure on its ventricular-facing surface. The passive assist cage 5365 provides a compressive resistance outward against the inner surface of the left atrium. During recovery, the passive assist cage 5265 provides an outward spring-like passive assist to the outward-moving cardiac atrial tissue.

LIST OF REFERENCES NUMBERS

100 prosthetic medical device tricuspid
102 elongated flexible cylinder (pliant tubular conduit)
104 cylinder channel/conduit lumen
106 top end
108 bottom end
110 internal surface
112 external surface
113 cylinder/conduit mid-segment side wall
114 top stent/resilient annular or subannular frame
116 top stent channel
118 top stent side wall
120 top stent top aperture
122 top stent bottom aperture
124 top stent cover
126 bottom stent/anchor nonperforating
128 top end of bottom stent
130 bottom end of bottom stent
132 side wall of bottom stent
134 2-5 tethers
136 conic cylinder
138 top edge of cylinder top end
140 top spacer segment of cylinder top end
142 stent mounting segment of cylinder top end
144 collar
846 collar leaflet anchors
148 deflatable ring
650 collar panel
952 annular tissue anchor
200 prosthetic medical device mitral
202 elongated flexible cylinder (pliant tubular conduit)
214 top stent/resilient annular or subannular frame
220 top stent top aperture
226 bottom stent/anchor nonperforating
234 2-5 tethers
400 prosthetic medical device
402 elongated flexible cylinder (pliant tubular conduit)
420 top stent top aperture
426 bottom stent/anchor nonperforating
434 2-5 tethers
444 supra-annular collar
500 prosthetic medical device
502 elongated flexible cylinder (pliant tubular conduit)
520 top stent top aperture
526 bottom stent/anchor nonperforating
534 2-5 tethers
544 supra-annular collar
600 prosthetic medical device
602 elongated flexible cylinder (pliant tubular conduit)
620 top stent top aperture
626 bottom stent/anchor nonperforating
634 2-5 tethers
644 supra-annular collar
650 partial atrial collar panel
700 prosthetic medical device
702 elongated flexible cylinder (pliant tubular conduit)
720 top stent top aperture
726 bottom stent/anchor nonperforating
734 2-5 tethers
744 supra-annular collar
750 panel shaped atrial collar panel
800 prosthetic medical device
802 elongated flexible cylinder (pliant tubular conduit)
844 supra-annular collar
846 wide-variety leaflet-collar anchors
900 prosthetic medical device
902 elongated flexible cylinder (pliant tubular conduit)
908 bottom end of conduit
914 sub-annular stent/frame
926 bottom stent/anchor nonperforating
934 2-5 tethers
940 top spacer segment
944 supra-annular collar
952 perivalvular leaflet anchors
1000 prosthetic medical device
1002 elongated flexible cylinder (pliant tubular conduit)
1044 supra-annular collar
1046 wide-variety leaflet-collar anchors
1100 prosthetic medical device
1102 elongated flexible cylinder (pliant tubular conduit)
1108 bottom end of conduit
1114 sub-annular stent/frame
1126 bottom stent/anchor nonperforating
1134 2-5 tethers
1140 top spacer segment
1144 supra-annular collar
1152 perivalvular leaflet anchors
1400 prosthetic medical device
1402 elongated flexible cylinder (pliant tubular conduit)
1414 sub-annular stent/frame
1426 bottom stent/anchor nonperforating
1434 2-5 tethers
1500 prosthetic medical device
1502 elongated flexible cylinder (pliant tubular conduit)
1514 sub-annular stent/frame
1526 bottom stent/anchor nonperforating
1534 2-5 tethers 1600 prosthetic medical device
1602 elongated flexible cylinder (pliant tubular conduit)
1614 sub-annular stent/frame
1626 bottom stent/anchor nonperforating
1634 2-5 tethers
1700 prosthetic medical device
1702 elongated flexible cylinder (pliant tubular conduit)
1714 sub-annular stent/frame
1726 bottom stent/anchor nonperforating
1734 2-5 tethers
1744 toroid collar
1800 prosthetic medical device
1802 elongated flexible cylinder (pliant tubular conduit)
1814 sub-annular stent/frame
1826 bottom stent/anchor nonperforating
1834 2-5 tethers
1844 toroid collar
1850 large panel
1900 prosthetic medical device
1902 elongated flexible cylinder (pliant tubular conduit)
1914 sub-annular stent/frame
1926 bottom stent/anchor nonperforating
1934 2-5 tethers
1944 toroidal collar
1950 large panel
2000 prosthetic medical device
2002 elongated flexible cylinder (pliant tubular conduit)
2014 sub-annular stent/frame
2026 bottom stent/anchor nonperforating
2034 2-5 tethers
2044 toroidal collar
2050 large panel
2100 prosthetic medical device
2102 elongated flexible cylinder (pliant tubular conduit)
2114 sub-annular stent/frame
2126 bottom stent/anchor nonperforating
2134 2-5 tethers
2140 top spacer
2144 toroidal collar
2147 compartment
2148 deflatable ring
2149 valve
2150 large panel
2200 prosthetic medical device
2202 elongated flexible cylinder (pliant tubular conduit)
2214 sub-annular stent/frame
2226 bottom stent/anchor nonperforating
2234 2-5 tethers
2244 toroidal collar
2250 large panel
2300 prosthetic medical device
2302 elongated flexible cylinder (pliant tubular conduit)
2314 sub-annular stent/frame
2326 bottom stent/anchor nonperforating
2334 2-5 tethers
2344 toroidal collar
2354 polymer matrix
2400 prosthetic medical device
2402 elongated flexible cylinder (pliant tubular conduit)
2404 channel
2414 sub-annular stent/frame
2426 bottom stent/anchor nonperforating
2434 2-5 tethers
2500 prosthetic medical device
2502 elongated flexible cylinder (pliant tubular conduit)
2504 channel
2514 sub-annular stent/frame
2526 bottom stent/anchor non-perforating
2534 2-5 tethers
2546 contralateral annular anchor
2600 prosthetic medical device
2602 elongated flexible cylinder (pliant tubular conduit)
2604 channel
2614 sub-annular stent/frame
2626 bottom stent/anchor non-perforating
2627 tissue anchor
2634 2-5 tethers
2646 contralateral annular anchor
2700 prosthetic medical device
2702 elongated flexible cylinder (pliant tubular conduit)
2704 channel
2714 sub-annular stent/frame
2726 bottom stent/anchor non-perforating
2734 2-5 tethers
2756 round perforations
2800 prosthetic medical device
2802 elongated flexible cylinder (pliant tubular conduit)
2804 channel
2814 sub-annular stent/frame
2826 bottom stent/anchor non-perforating
2834 2-5 tethers
2856 window pane perforations
2902 pliant tubular conduit
2904 aperture
2926 bottom anchor
2934 tethers
2944 central stent hub
2948 top toroidal inflatable ring
2949 bottom toroidal inflatable ring
2954 top (apical) circumferential flange
2956 bottom (ventricular) circumferential flange
3004 aperture
3044 central stent hub
3048 top toroidal inflatable ring
3054 top (apical) circumferential flange
3104 aperture
3144 central stent hub
3148 top toroidal inflatable ring
3149 bottom toroidal inflatable ring
3154 top (apical) circumferential flange
3156 bottom (ventricular) circumferential flange
3158 vacuum component
3214 top stent
3260 angular threading
3218 outer surface
3314 top stent
3360 rounded threading
3318 outer surface
3414 top stent
3460 first threading
3461 second threading
3418 outer surface
3514 top stent
3562 4 threads
3518 outer surface
3614 pear shape stent
3714 tapered stent
3763 full length threading
3718 outer surface
3864 compressed, unexpanded passive assist cage device
3865 uncompressed, expanded passive assist cage device
3866 balloon expanding delivery catheter
3867 balloon segment
3802 pliant tubular conduit 3902 conduit
3904 aperture
3965 uncompressed, expanded passive assist cage device
3970 right ventricular outflow tract outlet
4002 conduit
4004 aperture
4065 uncompressed, expanded passive assist cage device
4072 Semi-rigid conduit support
4102 conduit
4165 uncompressed, expanded passive assist cage device
4172 Semi-rigid conduit support
4202 conduit
4265 uncompressed, expanded passive assist cage device
4272 Semi-rigid conduit support
4302 conduit
4365 uncompressed, expanded passive assist cage device
4372 Semi-rigid conduit support
4605 prosthetic valve
4665 cage device
4673 vascular port
4705 prosthetic valve
4765 cage device
4773 vascular port
4805 prosthetic valve
4865 cage device
4873 vascular port
4905 prosthetic valve
4965 cage device
4973 vascular port
5005 prosthetic valve
5065 cage device
5073 vascular port
5105 prosthetic valve
5165 cage device
5173 vascular port
5205 prosthetic valve
5265 cage device
5273 vascular port
5305 prosthetic valve
5365 cage device
5373 vascular port.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. A prosthetic medical device, comprising:
(i) an elongated flexible cylinder defining a channel therein, said channel having a volume that ranges from 1.57 mL-18.84 mL, said cylinder having an average radius of 4.0-16.5 mm and an average height of 20-60 mm, said cylinder comprised of decellularized pericardium, said cylinder having top end, a bottom end, an internal surface, and an external surface, said cylinder is compressible under a pressure of 100-160 mm Hg on the external surface to close the channel, and said cylinder is expandable under a pressure of 40-80 mm Hg on the internal surface to open the channel;
(ii) a one-piece, laser-cut, expandable nitinol top stent, said top stent attached to the top end of the cylinder, said top stent shaped as a conic frustum when expanded and defining a top stent channel therein, said conic frustum having a side wall, a top aperture, and a bottom aperture, said side wall having an average side length of 5-20 mm, said top aperture having an average expanded diameter of 30-35 mm, said bottom aperture having an average expanded diameter of 40-60 mm, said top stent having a cover, said cover connected with the cylinder wherein the channel of the cylinder is in communication with the top stent channel; and
(iii) a one-piece, laser-cut, expandable nitinol bottom stent, said bottom stent having a top end, a bottom end, and a side wall, said top end of the bottom stent having from 2-5 tethers attached to the bottom end of the cylinder, said bottom stent having an average expanded diameter of 20-35 mm.

2. The prosthetic medical device of claim 1, wherein the cylinder is shaped as a conic cylinder, said top end having a diameter of 30-35 mm and said bottom end having a diameter of 8-20 mm.

3. The prosthetic medical device of claim 1, wherein the top stent cover is comprised of polyethylene terephthalate, decellularized pericardium, or a layered combination thereof.

4. The prosthetic medical device of claim 1, wherein the top end of the cylinder comprises, in order, a top edge connected to a top spacer segment that is connected to a top stent mounting segment, wherein the top edge has an collar mounted around the circumference of the top edge, said collar arranged as a flexible, semi-rigid, substantially flat panel or flat disk and having an average diameter of 30-60 mm, said collar having a nitinol frame covered with polyethylene terephthalate, decellularized pericardium, or a layered combination thereof, wherein the top spacer segment of the cylinder has a height from 5-20 mm, and wherein the top stent is mounted circumferentially around the top stent mounting segment of the cylinder.

5. The prosthetic medical device of claim 1, wherein the collar has one or more tissue anchors arranged along the circumference of the collar.

6. The prosthetic medical device of claim 1, wherein the nitinol frame of the collar supports a gel ring, wherein the gel ring is comprised of an expandable material enclosed within an outer sealing membrane, wherein the expandable material is a swellable powder within a polymeric matrix, a swellable polymeric matrix, or a swellable polymeric liquid.

7. The prosthetic medical device of claim 1, wherein the top stent comprises a covered nitinol frame that supports a deflatable ring, wherein the deflatable ring is comprised of a toroid-shaped sealed compartment having a valve, said sealed compartment fillable with a biocompatible liquid or gas, wherein upon removal of some or all of the biocompatible liquid or gas, the deflatable ring has a reduced diameter, and wherein upon removal of some or all of the biocompatible liquid or gas, the top spacer segment of the cylinder has a reduced height and the collar is compressed in the direction of the top stent.

8. The prosthetic medical device of claim 1, wherein the top stent has one or more tissue anchors arranged along the side wall of the top stent.

9. The prosthetic medical device of claim 1, wherein the bottom stent has one or more tissue anchors arranged along the side wall of the bottom stent.

10. The prosthetic medical device of claim 1, wherein the cylinder has an hourglass (hyperboloid) shape from top end to bottom end.

11. The prosthetic medical device of claim 1, wherein the bottom end of the cylinder is sealed, and wherein the cylinder has one or more perforations in a mid-segment side wall of the cylinder.

12. The prosthetic medical device of claim 1, wherein the device is compressed within a delivery sheath, said delivery sheath having a diameter of 5.0-6.0 mm.

13. The prosthetic medical device of claim 1, wherein the top stent comprises a central stent hub with aperture and having a top circumferential flange and a bottom circumferential flange connected to the hub, with a top toroidal inflatable ring attached to the top circumferential flange and a bottom toroidal inflatable ring attached to the bottom circumferential flange.

14. The prosthetic medical device of claim 1, wherein the top stent comprises a threaded structure on an exterior surface of the stent, wherein the threaded structure allows for a simple circular screw-type deployment of the device into a native annulus to aid in sealing and sizing of the top stent into the native annulus.

15. A method of controlling flow of bodily fluid within an enclosed cavity of a human body, said enclosed cavity having a reciprocating pressure differential, the method comprising the steps:

(i) delivering the prosthetic medical device of claim 1 to the enclosed cavity within the human body;

(ii) arranging the prosthetic medical device of claim 1 whereby the cylinder and cylinder channel are arranged parallel to a flow of fluid entering the enclosed cavity;

(iii) expanding the top stent within an entrance to the enclosed cavity to mount the top end of the cylinder within the entrance, and whereby the side wall of the top stent applies an axial compression force and seals the entrance;

(iv) expanding the bottom stent within the enclosed cavity to anchor the bottom end of the cylinder;

wherein bodily fluid arriving at the enclosed cavity is diverted into the channel of the cylinder;

wherein the reciprocating pressure differential comprises a low pressure state and a high pressure state;

wherein bodily fluid flows into the channel to the enclosed cavity during the low pressure state, and wherein bodily fluid is prevented from flowing into the channel to the enclosed cavity during the high pressure state, wherein the high pressure state exerts a force on the external surface of the cylinder and collapses the reversibly collapses the channel.

16. The method of claim 15, further comprising the step of anchoring the prosthetic medical device of claim 1 to tissue within the enclosed cavity.

\* \* \* \* \*